United States Patent
Yamanaka et al.

(10) Patent No.: US 7,170,213 B2
(45) Date of Patent: Jan. 30, 2007

(54) SURFACE ACOUSTIC WAVE ELEMENT, ELECTRIC SIGNAL PROCESSING APPARATUS USING THE SURFACE ACOUSTIC WAVE ELEMENT, ENVIRONMENT EVALUATING APPARATUS USING THE ELECTRIC SIGNAL PROCESSING APPARATUS, AND ANALYZING METHOD USING THE SURFACE ACOUSTIC WAVE ELEMENT

(75) Inventors: Kazushi Yamanaka, 6-3, Katsura 2-chome, Izumi-ku, Sendai-shi, Miyagi 981-3134 (JP); Noritaka Nakaso, Tokyo (JP); Yusuke Tsukahara, Tokyo (JP)

(73) Assignees: Toppan Printing Co., Ltd., Tokyo (JP); Kazushi Yamanaka, Sendai (JP)

( * ) Notice: Subject to any disclaimer, the term of this patent is extended or adjusted under 35 U.S.C. 154(b) by 0 days.

(21) Appl. No.: 10/819,365

(22) Filed: Apr. 7, 2004

(65) Prior Publication Data
US 2004/0189148 A1   Sep. 30, 2004

Related U.S. Application Data

(63) Continuation of application No. PCT/JP02/10477, filed on Oct. 9, 2002.

(30) Foreign Application Priority Data

Oct. 9, 2001 (JP) .............................. 2001-311788
Oct. 9, 2001 (JP) .............................. 2001-311789

(51) Int. Cl.
*H03H 9/64* (2006.01)
*H03H 9/25* (2006.01)

(52) U.S. Cl. ............................ 310/313 R; 310/313 A; 310/313 B; 310/313 C; 310/313 D

(58) Field of Classification Search ..... 310/313 A–313 R, 371, 368; 333/193
See application file for complete search history.

(56) References Cited

U.S. PATENT DOCUMENTS 3,815,056 A   6/1974   Meyer et al. ................ 333/150

(Continued)

FOREIGN PATENT DOCUMENTS

JP   8-68780   3/1996

(Continued)

OTHER PUBLICATIONS

Hideo Nishino et al., "Optical Probe Detection of High-Frequency Surface Acoustic Waves Generated by Phase Velocity Scanning of Laser Interference Fringes", Jpn. J. Appl. Phys., vol. 33 (1994), Part 1, No. 5B, May 1994, pp. 3260-3264.

*Primary Examiner*—Darren Schuberg
*Assistant Examiner*—J. Aguirrechea

(57) ABSTRACT

A surface acoustic wave element includes a single crystal base which has an annular surface formed by at least one portion of a spherical surface, and an exciting unit which excites a surface acoustic wave propagating along the annular surface. An electric signal processing apparatus includes the surface acoustic wave element, an input portion which inputs a predetermined signal to the exciting unit so that the wave is excited, a detecting unit which detects the propagating wave, and an output portion which outputs a signal corresponding to the wave detected by the detecting unit. An environment evaluating apparatus includes the processing apparatus, and a processing portion which evaluates an environment around the base, based on at least one of a frequency of the signal outputted by the processing apparatus, an intensity thereof, and time elapsing from a signal input time to a signal output time from the processing apparatus.

19 Claims, 9 Drawing Sheets

U.S. PATENT DOCUMENTS

| | | | |
|---|---|---|---|
| 6,052,517 A * | 4/2000 | Matsunaga et al. | 716/8 |
| 6,509,645 B2 * | 1/2003 | Tatsumi et al. | 257/738 |
| 6,679,118 B1 * | 1/2004 | Esashi et al. | 73/514.32 |
| 6,691,387 B2 * | 2/2004 | Hanafy | 310/367 |
| 2002/0014809 A1 * | 2/2002 | Tsukahara et al. | 310/313 R |
| 2003/0071540 A1 * | 4/2003 | Ito et al. | 310/313 R |

FOREIGN PATENT DOCUMENTS

| | | | |
|---|---|---|---|
| JP | 2002-26688 | | 1/2002 |
| JP | 2002-141769 | | 5/2002 |
| JP | 2005159580 A | * | 6/2005 |
| WO | WO 01/45255 A1 | | 6/2001 |

* cited by examiner

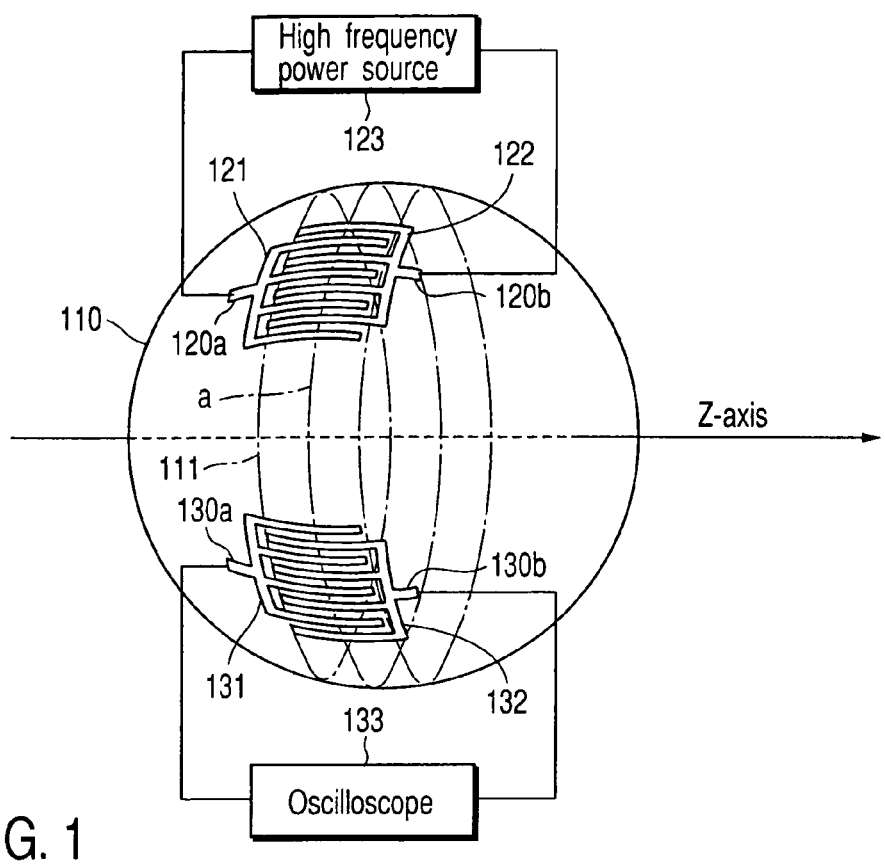
F I G. 1
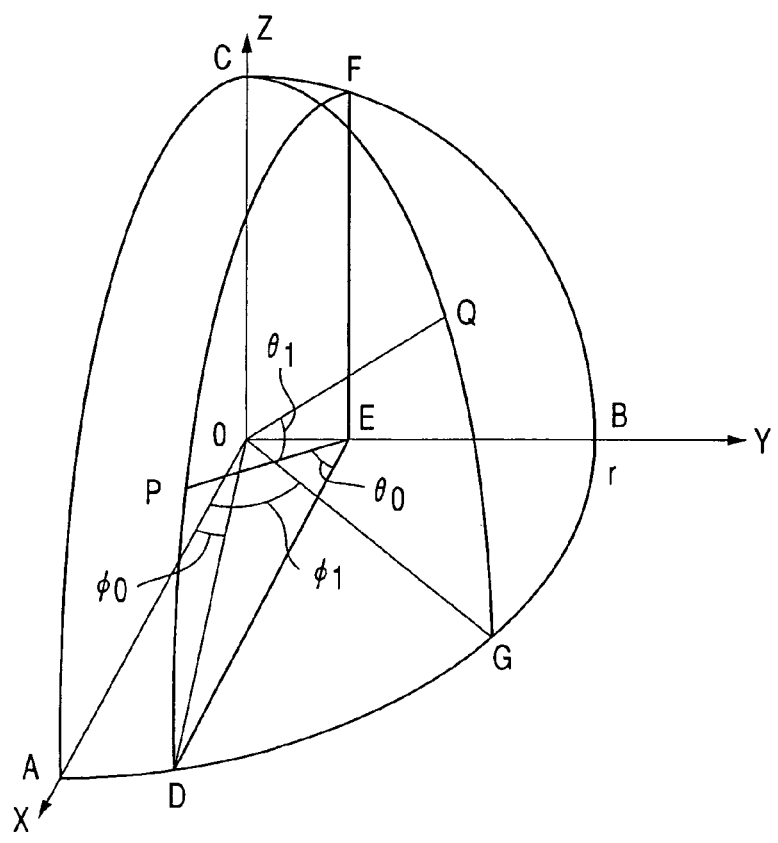
F I G. 2

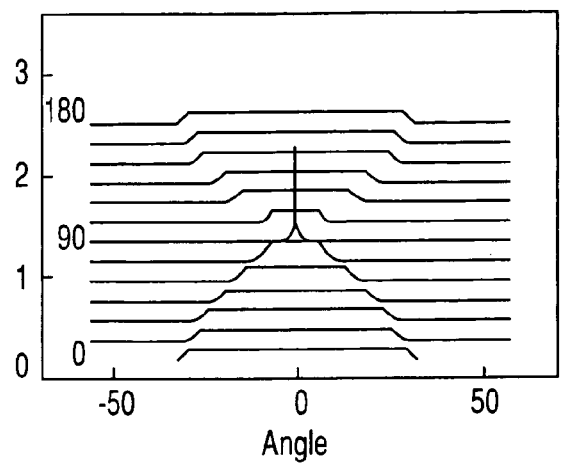
m=600, Opening half angle $\theta_A$=30deg
F I G. 3A
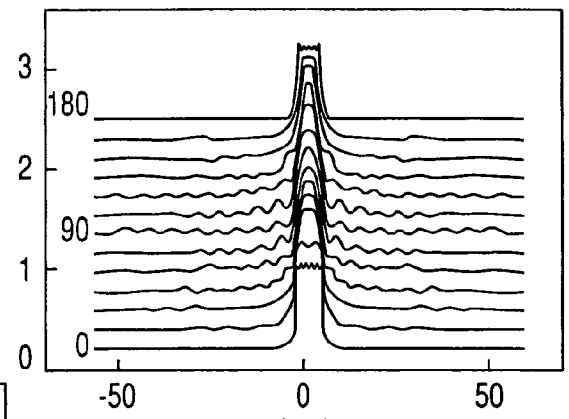
m=600, Opening half angle $\theta_A$=3.5deg
F I G. 3B
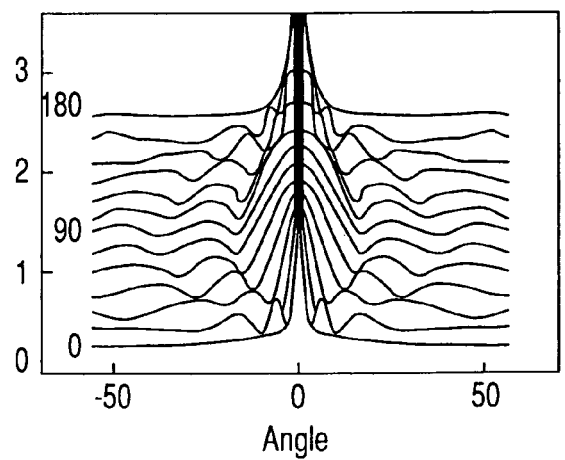
m=600, Opening half angle $\theta_A$=1deg
F I G. 3C
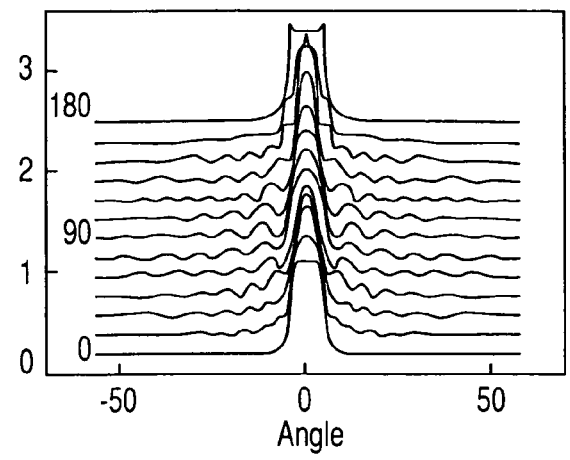
m=300, Opening half angle $\theta_A$=4.5deg
F I G. 3D

SURFACE ACOUSTIC WAVE ELEMENT, ELECTRIC SIGNAL PROCESSING APPARATUS USING THE SURFACE ACOUSTIC WAVE ELEMENT, ENVIRONMENT EVALUATING APPARATUS USING THE ELECTRIC SIGNAL PROCESSING APPARATUS, AND ANALYZING METHOD USING THE SURFACE ACOUSTIC WAVE ELEMENT

CROSS-REFERENCE TO RELATED APPLICATIONS

This is a Continuation Application of PCT Application No. PCT/JP02/10477, filed Oct. 9, 2002, which was not published under PCT Article 21 (2) in English.

This application is based upon and claims the benefit of priority from prior Japanese Patent Applications No. 2001-311788, filed Oct. 9, 2001; and No. 2001-311789, filed Oct. 9, 2001, the entire contents of both of which are incorporated herein by reference.

BACKGROUND OF THE INVENTION

1. Field of the Invention

The present invention relates to a surface acoustic wave element, an electric signal processing apparatus using the surface acoustic wave element, an environment evaluating apparatus using the electric signal processing apparatus, and an analyzing method which analyzes a material to be inspected by using the surface acoustic wave element.

2. Description of the Related Art

A surface acoustic wave element has been conventionally well known as an element which generates a surface acoustic wave on a base member, and which receives the surface acoustic wave generated on the base member.

In the conventional surface acoustic wave element, a pair of comb-shaped electrodes is provided on a flat base member. The base member is made of a piezoelectric material or a piezoelectric member is provided between the comb-shaped electrode and the base member. And, a surface acoustic wave is excited by applying a high frequency voltage to one of the comb-shaped electrodes, in the direction in which the electrode pieces of the comb-shaped electrode are arranged. Another comb-shaped electrode is disposed in the direction of propagation of the surface acoustic wave, and receives the surface acoustic wave.

The surface acoustic wave element is used for a delay line, an oscillating element or a resonating element for a transmitter, a filter for selecting frequencies, a chemical sensor, a biosensor, a remote tag, or the like.

In order to improve the performance of such a surface acoustic wave element, it is required to reduce the propagation loss as much as possible when the surface acoustic wave propagates between two pairs of comb-shaped electrodes.

However, in the usual surface acoustic wave element, since the surface of the piezoelectric material member or the surface of the base member, on either one of which the pair of comb-shaped electrodes are provided, is flat, the surface acoustic wave excited by one of the comb-shaped electrodes is diffused in a direction perpendicular to the propagating direction of the surface acoustic wave on the above-described flat surface while the surface acoustic wave is propagating toward another comb-shaped electrode, and is weakened. Therefore, the propagation loss of the surface acoustic wave cannot be reduced. This means that, in a case where the change in time passed from the transmission to the receipt of the surface acoustic wave is observed as a measuring object and is used for something, it is difficult to obtain a sufficient result from the observation because the propagation loss becomes larger as the propagation distance becomes longer. Due to these problems, the performance of the surface acoustic wave element can not be made to high.

In order to solve such problems, use of a spherical base member has been considered. When a surface acoustic wave is excited on the spherical surface of the base member, the surface acoustic wave is not diffused, and propagates around the base member a large number of times. This realizes a long propagation of the surface acoustic wave with no diffuse.

However, when the spherical base member is used, it is necessary to form comb-shaped electrodes or the like in order to apply an electric field on the surface of the base member. And, a photolithography method must be used to form a pattern which is less than 0.5 mm. This method increases the number of steps in a manufacturing process for spherical surface acoustic wave element, and increases the manufacturing cost thereof.

Further, when the electrodes made of such as metal or the like are directly formed on the surface of the base member, the surface acoustic wave which propagates around the surface of the base member is reflected by the electrodes, so that the intensity of the surface acoustic wave is rapidly reduced as the number of the round of the wave increases. Therefore, even if a sufficient and accurate evaluation needs to carry out a measurement of the time passed while the wave propagates around the base member 30 times, the surface acoustic wave is attenuated or diffused while the wave propagates around the base member about 20 times, and the evaluation cannot be carried out sufficiently and accurately.

Further, when the base member is not made of a piezoelectric material, it is necessary to provide a film of a piezoelectric material on the surface of the base member. However, since the propagation characteristic of the surface acoustic wave varies upon the thickness of this film, it is difficult to manufacture a large number of the elements. Moreover, when the base member is made of a piezoelectric material, a single crystal such as quarts, $LiNbO_3$, $LiTaO_3$, or the like is appropriate as a fine piezoelectric material. However, it has been difficult to realize the base member made of the single crystal because the propagation velocity of the surface acoustic wave changes while the wave propagates on the surface of the single crystal and the surface acoustic wave can not propagate around thereon.

An object of the present invention is to provide a surface acoustic wave element which can realize an extremely large number of propagation of the surface acoustic wave around a spherical base member and can carry out highly accurate signal processing and its evaluation. Another object of the present invention is to provide a surface acoustic wave element which uses a base member made of a piezoelectric material so that a surface acoustic wave can efficiently propagate on the surface of the base member. Further object of the present invention is to provide an electric signal processing apparatus using the surface acoustic wave element, and to provide an environment evaluating apparatus using the electric signal processing apparatus. More further object of the present invention is to provide an analyzing method in which a material to be inspected is analyzed by using the surface acoustic wave element.

BRIEF SUMMARY OF THE INVENTION

A surface acoustic wave element comprises: a base member which has an annular surface formed by at least one portion of a spherical surface and continuing annularly, and which is made of a single crystal; and a surface acoustic wave exciting unit which excites a surface acoustic wave propagating along the annular surface.

Further, a surface acoustic wave element comprises: a base member which has an annular surface formed by at least one portion of a spherical surface and continuing annularly, and at least one portion of which is made of a piezoelectric material; and a surface acoustic wave exciting unit which excites a surface acoustic wave propagating along the annular surface, the surface acoustic wave exciting unit facing the annular surface with a gap therebetween.

An electric signal processing apparatus comprises: any one of the surface acoustic wave elements described above; an input portion which inputs a predetermined electric signal to the any one of the surface acoustic wave elements so that a surface acoustic wave propagating along the annular surface is excited by the surface acoustic wave element; a detecting unit which detects the surface acoustic wave propagating along the annular surface; and an output portion which outputs an electric signal corresponding to the surface acoustic wave detected by the detecting unit.

An environment evaluating apparatus comprises: the electric signal processing apparatus described above; and a processing portion which evaluates an environment around the base member or an environment in which the base member is placed, on the basis of at least one of a frequency of the electric signal outputted by the electric signal processing apparatus, an intensity of the electric signal, and time elapsing from the time when an electric signal is inputted to the electric signal processing apparatus to the time when an electric signal is outputted by the electric signal processing apparatus.

An analyzing method comprises: a base member preparing step in which a base member is prepared, the base member having an annular surface formed by at least one portion of a spherical surface and continuing annularly, and a reacting portion which is formed along the annular surface and reacts with a material to be inspected; a reacting step in which the reacting portion reacts to the material to be inspected; a propagating step in which a surface acoustic wave is propagated along the annular surface; and a detecting step in which the surface acoustic wave propagated in the propagating step is detected.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 shows a structure of a surface acoustic wave element of a first embodiment according to the present invention, and a structure of an electric signal processing apparatus using the surface acoustic wave element.

FIG. 2 shows a coordinate system used for calculating an amplitude of a surface acoustic wave.

FIGS. 3A, 3B, 3C and 3D schematically show four states in which the surface acoustic waves obtained by changing a wave number parameter "m" (a ratio of a wavelength of the surface acoustic wave to a length of the circumference) calculated by a formula prepared by using the coordinate system of FIG. 2, and by changing an opening half angle (½ of a width at which vibrating means is provided), propagates on the surface of a spherical base member.

DETAILED DESCRIPTION OF THE INVENTION

Figure 4:
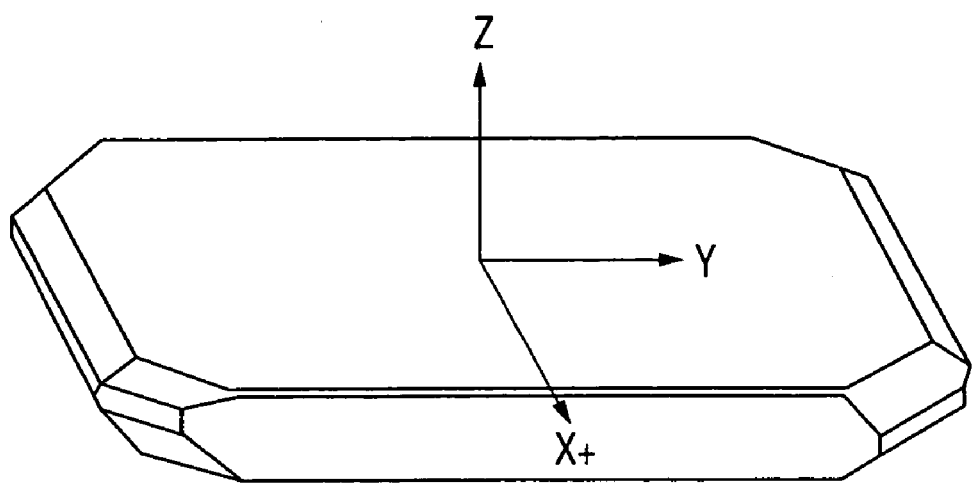
FIG. 4 shows crystal axes of quarts.

In the followings, surface acoustic wave elements according to embodiments of the present invention, electric signal processing apparatuses using the surface acoustic wave elements according to the embodiments of the present invention, an environment evaluating apparatus using one electric signal processing apparatus according to one embodiment of the present invention, and an analyzing method using one surface acoustic wave element according to one embodiment of the present invention will be described with reference to FIGS. 1 to 16B.

At first, a surface acoustic wave element of a first embodiment according to the present invention and an electric signal processing apparatus using the surface acoustic wave element of the first embodiment will be described.

FIG. 1 shows a structure of the surface acoustic wave element and the electric signal processing apparatus using the surface acoustic wave element. The surface acoustic wave element has a spherical base member 110 made of a single crystal. In this embodiment, quarts is used for the single crystal. However, a single crystal of a trigonal system such as LiNbO$_3$, LiTaO$_3$, or the like may be used.

A pair of comb-shaped electrode pieces 121, 122 connected to a high frequency power source 123 are provided on the surface of the base member 110. The comb-shaped electrode pieces 121, 122 are used as a surface acoustic wave exciting means. The base member 110 and the comb-shaped electrode pieces 121, 122 configure the surface acoustic wave element. The high frequency power source 123 outputs a predetermined electric signal. Each of the comb-shaped electrode pieces 121, 122 has a chromium layer laminated on the surface of the base member 110 and a gold layer laminated on the chromium layer, and is formed by using photolithography. Input terminals 120a, 120b connected to the high frequency power source 123 are provided at the comb-shaped electrode pieces. The input terminals 120a, 120b are used as an input portion. The input terminals 120a, 120b input the predetermined electric signal from the high frequency power source 123 into the comb-shaped electrode pieces 121, 122. As a result, as will be described hereinafter, the comb-shaped electrode pieces 121, 122 excite a surface acoustic wave which corresponds to the electric signal and propagates along an annular portion of the surface of the base member 110.

The base member 110 of quarts is a piezoelectric material. That is, the surface of the base member 110 is made of a piezoelectric material. When a voltage is applied to the comb-shaped electrode pieces 121, 122 by the high frequency power source 123, the surface of the base member 110 vibrates due to the piezoelectric effect, and a surface acoustic wave of a predetermined mode is excited on the surface of the base member 110. The surface acoustic wave exciting means using the comb-shaped electrode pieces 121, 122 can excite the surface acoustic wave with a relatively high efficiency and in a specific direction.

The excited surface acoustic wave propagates along the annular surface portion 111 of the base member 110 continuing in an annular shape. The surface acoustic wave orbits the annular surface portion of the base member 110. Detecting means which detects the surface acoustic wave propagating along the annular surface portion 111 is provided on the annular surface portion 111. In the present embodiment, comb-shaped electrode pieces 131, 132 other than the comb-shaped electrode pieces 121, 122 are used as the detecting means. The comb-shaped electrodes 131, 132 for detection detect the surface acoustic wave by converting the surface acoustic wave into an electric signal. Output terminals 130a, 130b for outputting the electric signal corresponding to the surface acoustic wave detected by the comb-shaped electrode pieces 131, 132 are provided at the comb-shaped electrode pieces 131, 132 for detection. The output terminals 130a, 130b are used as an output portion. An oscilloscope 133 is connected to the output terminals 130a, 130b through a predetermined circuit. The surface acoustic wave element, the input terminals 120a and 120b, the comb-shaped electrodes 131, 132 for detection, and the output electrode pieces 130a, 130b configure the electric signal processing apparatus. Note that, in addition to the comb-shaped electrode pieces 131, 132 for detection and the comb-shaped electrode pieces 121, 122 for excitation, a desired pattern for changing the propagation of the surface acoustic wave may be formed on the annular surface portion of the base member 110.

In this specification, an elastic wave propagating by concentrating energy at the vicinity of the surface of a base member of a single crystal is generically called as a surface acoustic wave. Further, the surface acoustic wave includes elastic waves called as a leakage elastic wave propagating while emitting energy from the base member of the single crystal, an SH (share-horizontal) wave, and a lateral wave.

It has been known that the phenomenon that the surface acoustic wave propagates along the annular surface portion of the spherical base member can be caused on a base member made of an isotropic material. But, on a base member made of a single crystal, the propagation velocity of the surface acoustic wave changes in accordance with the crystal orientation. Further, on the spherical base member made of the single crystal, it has been considered that the surface acoustic wave loses its energy and the propagation efficiency of the surface acoustic wave is lowered at every time when the surface acoustic wave propagates around the base member, because the surface acoustic wave passes through a crystal face at which the propagation of the surface acoustic wave is impossible, and passes through a crystal face at which the energy of the surface acoustic wave is diffused, while the surface acoustic wave propagates on the spherical body member.

However, the inventors of this invention and others found the following fact through experiments. That is, the above described phenomenon that the surface acoustic wave propagates along the annular surface portion of the spherical base member can be caused on a spherical base member made of a single crystal of a trigonal system such as quarts, LiNbO$_3$, LiTaO$_3$, or the like, if a route on which the surface acoustic wave propagates is appropriately selected. And, the route is determined by the crystal orientation as will be shown later. A large number of propagation of the surface acoustic wave can be achieved on the route because the dissipation of elastic wave energy and the reflection of the surface acoustic wave on the spherical surface are little when the surface acoustic wave propagates on the route.

When the base member is made of a non-piezoelectric material, it is necessary to form a piezoelectric film between the base member and the comb-shaped electrode pieces. However, since the base member of this embodiment is made of the single crystal such as quarts, LiNbO$_3$, or LiTaO$_3$, those of which are good piezoelectric materials, the base member of this embodiment does not need the piezoelectric film which makes the manufacturing cost of this surface acoustic wave element increase. Further, the base member of this embodiment without the piezoelectric film can be manufactured stably and speedy because the piezoelectric film changes the characteristic of the surface acoustic wave element on a basis of the thickness of the film, the thickness being changeable in accordance with a change in a condition of forming process for the film.

The purity of signal obtained by the base member of the single crystal such as quarts, LiNbO$_3$, or LiTaO$_3$ is higher than that obtained by the base member of the non-piezoelectric material. Accordingly, the surface acoustic wave element using the base member of the single crystal such as quarts, LiNbO$_3$, or LiTaO$_3$ has a performance which is more higher than that obtained by the surface acoustic wave element using the base member of the non-piezoelectric material.

In the above-described single crystals, quarts is extremely useful because it has high hardness, is easily machined and can be purchased inexpensively. Further, LiNbO$_3$ and LiTaO₃ have a high electrical/mechanical coupling coefficient, and have a low temperature dependency of the phase velocity of the surface acoustic wave so that they realize a good round of the propagation of the surface acoustic wave without noise.

Conditions under which the surface acoustic wave propagates around the surface of the spherical base member without being diffused were approximately determined as follows. The following calculations will be described in a case where the base member is made of an isotropic material. However, the approximate determination of the above described conditions can be obtained theoretically only in a case where the phase velocity of the surface acoustic wave in the surface acoustic wave propagating direction will not change markedly at the portion of the surface of the spherical base member on which the surface acoustic wave propagates.

At first, a case where the source of generation of the surface acoustic wave can be considered as a point will be described. The source of generation is on the surface of the base member. This corresponds to a fact that the overlapping width of the comb-shaped electrode pieces 121, 122 is less than ¹⁄₁₀₀ of the radius of the spherical surface of the base member 110. Here, the overlapping width is a length in which each of the comb-shaped electrode pieces 121 and each of the comb-shaped electrode pieces 122 face one another. It is clear that the overlapping width generally corresponds to the width of the surface acoustic wave excited by the comb-shaped electrode pieces 121, 122.

The surface acoustic wave generated at the point of the spherical surface of the base member firstly diverges in a concentric annular shape from the point on the spherical surface, and thereafter, the wave converges in the concentric annular shape toward a point of the spherical surface of the base member which is positioned oppositely to the wave generation point, and focuses on the opposite point. The wave converged on the opposite point further diverges from the opposite point in the concentric annular shape and then converges toward the wave generation point. This means that the surface acoustic wave generated at the point of the spherical surface of the base member has no specific direction of its propagation and diverges so that it is scattered by wiring attaching portions of the comb-shaped electrode pieces, the circuit patterns for the comb-shaped electrode pieces, and supporting portions for supporting the base member.

Next, a case where the source of generation of the surface acoustic wave can be considered as being a circular arc will be described. This corresponds to a fact that the overlapping width of the comb-shaped electrode pieces 121, 122 is greater than or equal to ¹⁄₁₀₀ of the radius of the spherical surface of the base member 110. However, the overall width of the comb-shaped electrode pieces including electric circuit patterns for the electrodes or the like must be less than or equal to half of the circumference length of the spherical surface of the base member 110, so that the overlapping width of the comb-shaped electrode pieces 121, 122 is less than or equal to half of the diameter of the spherical surface of the base member 110. FIG. 2 shows a coordinate system in which the center of the spherical base member is an origin "O" of the system. The points of intersection between the X, Y, and Z-coordinate axes and the spherical surface of the base member are respectively designated by "A", "B", and "C", and the spherical surface has a radius "r". Further, a point on the Y-axis between "O" and "B" is designated by "E", the point of intersection between a straight line which passes through the point E and is parallel to the Z-axis and the above-described spherical surface is designated by "F", and the point of intersection between a straight line which passes through the point E and is parallel to the X-axis and the above-described spherical surface is designated by "D". And, it is supposed that the surface acoustic wave is generated at a point "P" on the circular arc "DF" and reaches a point "Q" on the circular arc "CG". Here, a point "G" is located on the circular arc "AB". If angles $\phi_0$, $\theta_0$, $\phi_1$, $\theta_1$ are taken as shown in FIG. 2, the coordinates of the points "P" and "Q" are respectively (r cos $\phi_0$ cos $\theta_0$, r sin $\phi_0$, r cos $\phi_0$ sin $\theta_0$) and (r cos $\phi_1$ cos $\theta_1$, r cos $\theta_1$ sin $\phi_1$, r sin $\theta_1$).

Therefore, $$PQ^2 = 2r^2[1 - \cos\phi_0 \cos\theta_0 \cos\phi_1 \cos\theta_1 - \sin\phi_0 \cos\phi_1 \cos\theta_1 - \cos\phi_0 \sin\phi_0 \sin\theta_1] \quad (1).$$

Accordingly, provided that the corner POQ=$\theta$, the relationship of:

$$\cos\theta = \cos\phi_0 \cos\theta_0 \cos\phi_1 \cos\theta_1 + \sin\phi_0 \cos\phi_1 \cos\theta_1 + \cos\phi_0 \sin\phi_0 \sin\theta_1 \quad (2)$$

is established from the cosine rule.

The radial component of particle displacement of the surface acoustic wave at the point "Q", the surface acoustic wave being generated at the point P, is $$u_r = R_e \left[ \frac{C}{\sqrt{\sin\theta}} \exp\left\{ im\left(\theta - \frac{C_R t}{r}\right) \right\} \right] \quad (3)$$

(Viktorov, Rayleigh and Lamb Waves). Although the formula (3) is determined with respect to the Rayleigh wave and the Lamb wave, it can also be applied to general surface acoustic waves. Note that, here, "C" is a constant, "$C_R$" is a velocity of the Rayleigh wave, and "t" is time.

m=the length of the circumference/the wavelength of the surface acoustic wave, and "m" is called as a wave number parameter.

The angle "$\theta$" is determined from the formula (2). When the sound source has a circular arc shape the angle of which is 2$\theta_A$ from the point "E", the sound field of the point "Q" is obtained by integrating the formula (3) from $-\theta_A$ to $\theta_A$ with respect to $\theta_0$. The distribution of the sound field can be determined by calculating the formula (3) with changing an angle $\theta_1$ of elevation.

FIGS. 3A, 3B, 3C, and 3D show four states of propagation of the surface acoustic wave on the spherical surface, which is determined by using formula (3) when the point P is located on the "XZ" plane and $\phi_0$=0.

FIGS. 3A, 3B, and 3C show the sound fields (the dependency of the absolute value of particle displacement on the angle $\theta_1$) when the wave number parameter "m"=600. In the respective figures, the lowest plot shows a sound field when the angle $\phi_1$ of the propagation (propagation angle) of the surface acoustic wave on the spherical surface is 0°, and the sound fields when the angle $\phi_1$ increases by 15° at a time are successively plotted in the upward direction.

FIG. 3A shows the change of the sound field as the propagation angle $\phi_1$ increases in a case where an opening half angle $\theta_A$=30°. In this case, as is clear from FIG. 3A, the sound field firstly converges and then diverges as the propagation angle $\phi_1$ increases. That is, the width of the sound field reduces as the propagation angle $\phi_1$ increases from 0°, becomes minimum at the propagation angle $\phi_1=90°$, increases as the propagation angle $\phi_1$ increases beyond 90°, and becomes the same as that at the propagation angle $\phi_1=0°$, at the propagation angle $\phi_1=180°$. Hereinafter, the above-described change of the width of the sound field are repeated at every 180° of the propagation angle $\phi_1$ endlessly even if the number of propagation of the surface acoustic wave around the spherical surface becomes large. This is a specific phenomenon generated only on the spherical surface on which diffusion of waves by diffraction will not be caused. In this case, the width of the sound field will not increase over the opening half angle $\theta_A=30°$, and the energy of the surface acoustic wave is confined within a strip-shaped portion of $\theta_1<\theta_A$ on the spherical surface. In this case, even if any other object comes into contact with a portion of $\theta_1>\theta_A$ on the spherical surface, disturbance of the sound field will not be caused.

FIG. 3C shows a case where the opening half angle $\theta_A=1°$. In this case, as is clear from FIG. 3C, the change of the width of the sound field as the propagation angle $\phi_1$ increases is the same as that in the case where the opening half angle $\theta_A=0°$, or the surface acoustic wave is generated at a point on the spherical surface. In this case, the width of the sound field increases as the propagation angle $\phi_1$ increases from 0°, becomes maximum at the propagation angle $\phi_1=90°$, decreases as the propagation angle $\phi_1$ increases beyond 90°, and becomes the same as that at the propagation angle $\phi_1=0°$, at the propagation angle $\phi_1=180°$. In contrast to the case described above with reference to FIG. 3A, the energy of the surface acoustic wave in this case will not be confined within the strip-shaped portion of $\theta_1<\theta_A$ on the spherical surface and the energy spreads all over the spherical surface at the propagation angle $\phi_1=90°$. In this case, if any other object comes into contact with a portion of $\theta_1>\theta_A$ on the spherical surface at the propagation angle $\phi_1=90°$, disturbance of the sound field is caused.

FIG. 3B shows a case where the opening half angle $\theta_A=3.5°$. In this case, as is clear from FIG. 3B, the width of the sound field does not change as the propagation angle $\phi_1$ increases, and the surface acoustic wave propagates in a shape of collimated beam. That is, the energy of the surface acoustic wave in this case is confined within the strip-shaped portion of $\theta_1=\theta_A$ on the spherical surface. This is the same characteristic as that of Bessel beam in an infinite medium. And, the opening half angle $\theta_A$ by which the propagation of the surface acoustic wave in the shape of collimated beam can be obtained is called as a collimating angle $\theta_{col}$.

As is clear from FIGS. 3A, 3B, and 3C, when the opening half angle $\theta_A$ is substantially equal to the collimating angle $\theta_{col}$, the energy of the surface acoustic wave is confined within the narrowest strip portion on the spherical surface.

Moreover, the numerical analysis which is the same as described above is carried out with a change of the wave number parameter "m", and it is found that the collimating angle $\theta_{col}$ varies in accordance with the wave number parameter "m". FIG. 3D shows that, in a case where the wave number parameter "m" is 300, the surface acoustic wave propagates in the shape of the collimated beam when the opening half angle $\theta_A$ is substantially 4.5°. This means that the collimating angle $\theta_{col}$ in this case is about 4.5°.

Hereinafter, values of the collimating angle $\theta_{col}$ when the wave number parameter "m" is changed are shown.

| Wave number parameter "m" (Circumferential length of sphere/wavelength of surface acoustic wave) | Collimating angle $\theta_{col}$ |
|---|---|
| 150 | 7.0 |
| 300 | 4.5 |
| 450 | 4.0 |
| 600 | 3.5 |
| 750 | 3.0 |

Note that these values of Collimating angle $\theta_{col}$ are approximate values resulted from the numerical calculation by using the formula (3) with a change of the wave number parameter "m".

Now, referring back to FIG. 1, the surface acoustic wave element of this embodiment will be described again. When the surface acoustic wave is outputted from the comb-shaped electrode pieces 121, 122, the surface acoustic wave propagates along the annular surface portion 111 as described above. In order to ease the following explanation, the width of the annular surface portion 111 is set to be equal to the overlapping width of the comb-shaped electrode pieces 121, 122. The overlapping width of the comb-shaped electrode pieces 121, 122 is greater than or equal to the width of the source at which the surface acoustic wave is generated, the width of the source being determined by the collimating angle $\theta_{col}$. More preferably, the overlapping width is equal to the width determined by the collimating angle $\theta_{col}$. And, as is apparent from the result of the above-described numerical calculation, the surface acoustic wave propagates along the annular surface portion 111 without being diffused beyond of the width of the annular surface portion 111. When the surface acoustic wave is excited to have a width equal to the width determined by the collimating angle $\theta_{col}$ or to have a width approximate to the width determined by the collimating angle $\theta_{col}$, excess concentration and scattering of energy will not be caused within the annular surface portion 111. FIGS. 3A and 3B show the states of the propagations of the surface acoustic waves excited as described above. Typical values of the wave number parameter "m" which determines the collimating angle $\theta_{col}$ fall within a range from 100 to 800.

The above-described numerical calculation is performed under the condition in which the wavelength and the phase velocity of the surface acoustic wave are constant on all over the place of the spherical surface on which the surface acoustic wave propagates. However, actually, the wavelength and the phase velocity of a surface acoustic wave changes in accordance with the crystal orientation of the single crystal on a spherical base member made of quarts of a single crystal, even if the frequency of the surface acoustic wave is constant. This mean that actually the wave number parameter "m" is not constant on the spherical base member. But, for the above-described numerical calculation, it is assumed that the wave number parameter "m" is constant on the spherical base member. And, the wave length of the surface acoustic wave excited by the surface acoustic wave exciting means on the annular surface portion of the base member on which the surface acoustic wave propagates is used to determine the constant wave number parameter "m". That is, the wavelength of the surface acoustic wave propagated on the annular surface portion of the base member on which the comb-shaped electrode pieces 121, 122 are provided is used to determine the parameter "m". Further, it is preferable that the shape of the pattern of each comb-shaped electrode pieces 121, 122 is so set to excite the surface acoustic wave which has a predetermined wavelength for propagating the wave on and within the portion of the base member on which the comb-shaped electrode pieces 121, 122 are provided.

The annular surface portion 111 on which the surface acoustic wave propagates can be set along any one of predetermined routes determined in accordance with the crystal orientation of the single crystal forming the base member 110 as described above. These routes on quarts of the single crystal belonging to the trigonal system are verified through experiments by the inventors or others. These routes relate to the Z-axis of quarts of the single crystal. The crystal axes of quarts of the single crystal are shown in FIG. 4.

Figure 5:
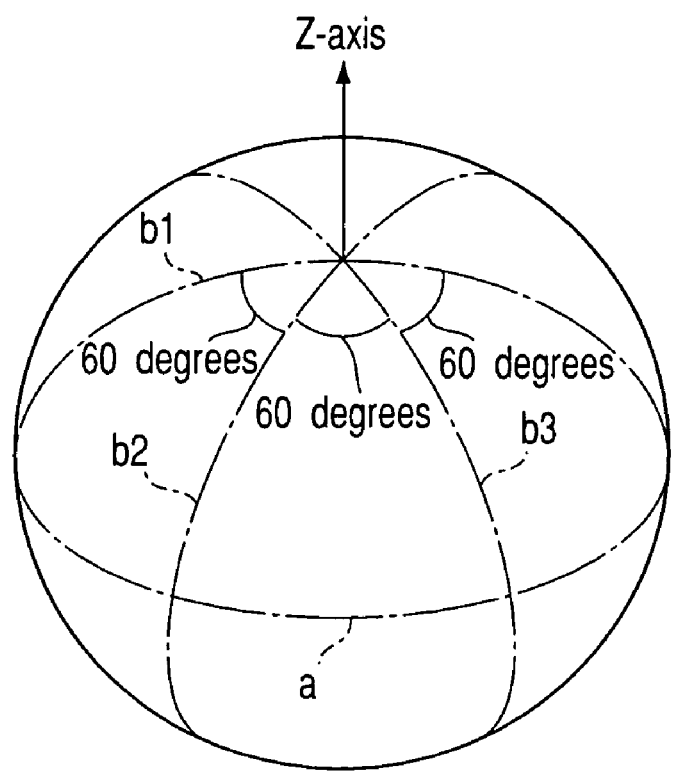
FIG. 5 shows routes on each of which the surface acoustic wave can propagates.

FIG. 5 shows these routes. In order to ease explanation, it is supposed that the Z-axis passes through the center of the spherical base member 110. These routes determined in accordance with the crystal orientation include four routes "a", "b1", "b2", and "b3". The route "a" is an intersection line along which the spherical surface of the base member 110 and a plane passing through the center of the spherical surface and crossing the Z-axis at 90 degrees thereto intersect with each other. Each of the routes "b1", "b2", and "b3" is an intersection line along which the spherical surface of the base member 110 and one of three planes passing through the center of the spherical surface and being in parallel to the Z-axis intersect with each other. The plane including the route "b1" crosses with each of the planes including the routes "b2" and "b3" at 60 degrees thereto. If it is supposing that the spherical base member 110 is the earth and the Z-axis is the geographic axis of the earth, the route "a" is considered as the equator, and the routes "b1", "b2", and "b3" are considered to be structured by combining six lines of longitude which are arranged at an interval of 60°.

In this embodiment, the surface acoustic wave propagates along the route "a" as shown in FIG. 1. That is, the annular surface portion 111 is formed along the route "a". However, the present invention is not limited thereto. The surface acoustic wave may be propagated along at least two routes among the routes "a", "b1", "b2", and "b3". For example, in order to propagate the surface acoustic wave along the route "a" and the route "b1", the surface acoustic wave exciting means are respectively provided on the routes "a" and "b1". Alternatively, the surface acoustic wave exciting means is provided only on the route "a", and a scatterer which scatters the surface acoustic wave or a reflector which reflects the surface acoustic wave is provided on a cross point at which the route "a" and the route "b1" cross each other on the base member 110. In this case, the scatterer or the reflector makes the surface acoustic wave propagating along the route "a" branch into the route "b1". And, if the scatterer or the reflector does not scatter the surface acoustic wave propagating along the route "a" to an extent which affect the propagation of the wave along the route "a", the surface acoustic wave excited on and propagating along the route "a" can be detected in an outside of the route "a".

Figure 6:
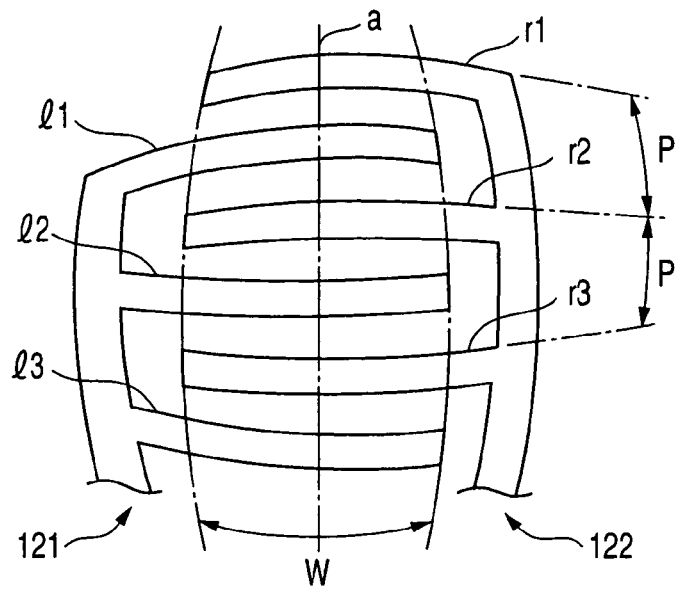
FIG. 6 is a plan view of a comb-shaped electrode of the surface acoustic wave element in the first embodiment of the present invention.

Then, the comb-shaped electrode pieces 121, 122 will be described in more detail. FIG. 6 is a plan view of the comb-shaped electrode pieces 121, 122. The comb-shaped electrode piece 121 has a plurality of branches 11, 12, 13, ... arranged in a direction in which the surface acoustic wave propagates. The comb-shaped electrode piece 122 has a plurality of branches r1, r2, r3, ... which are arranged alternately with the branches 11, 12, 13, .... All gaps of the adjacent branches (for example, the gap between the branch r1 and the branch 11, or the gap between the branch 11 and the branch r2) are the same as to each other. The branches 11, 12, 13, ... and the branches r1, r2, r3, ... extend to be perpendicular to the route "a". That is, in the above described case in which the Z-axis of the base member 110 is supposed as the geographic axis of the earth, these branches extend along the longitude lines. These branches are arranged periodically. Thus, if the branches 11 and r1 can be moved along the route "a", the branches 11 and r1 can overlap with the branches 12 and r12, and with the branches 13 and r3, .... The branches 11 and r1 form a unit of the branches which are arranged periodically. If the unit of the branches are arranged in the direction in which the surface acoustic wave propagates, the comb-shaped electrode pieces 121, 122 are formed.

A cycle "P", which is a length of the unit of the branches in the direction in which the surface acoustic wave propagates, is constant. The wavelength of the surface acoustic wave excited by the surface acoustic wave exciting means is less than or equal to 1/10 of the radius of the spherical surface of the base member. In this case, the wavelength is not the same as that of the characteristic vibration of the base member 110, but is substantially equal to the cycle "P". However, as described above, in some cases, the wave length of the surface acoustic wave excited by the surface acoustic wave exciting means such as the comb-shaped electrode pieces 121, 122 changes depending on a position of the portion on the base member 110, on that portion the surface acoustic wave exciting means such as the comb-shaped electrode pieces 121, 122 being provided.

The position of the portion on the base member 110, on that portion the comb-shaped electrode pieces 121, 122 being provided, is on the route "a" as shown in FIG. 1. The comb-shaped electrode pieces 121, 122 are arranged on the route "a" so that the surface acoustic wave excited by the comb-shaped electrode pieces 121, 122 propagates along the route "a". The route "a" can be determined on the basis of the Z-axis found by using X-ray diffraction or the like.

The cycle "P" is determined as follows. But, the following explanation is for a case in which only the surface acoustic wave of 15.1 MHz is excited and is propagated around the spherical body member 110. The cycle "P" can be determined by dividing a typical value of the phase velocity "3160 m/s" of the surface acoustic wave on the surface of quarts of the single crystal by its frequency. That is:

$$3160 \ (m/s)/15.1 \ (MHz) = 209.3 \ \mu m$$

In order to determine the cycle "P" for precisely and accurately outputting the surface acoustic wave of the predetermined frequency, firstly the X-axis or the Y-axis of the crystal orientation is found. Next, the theoretical phase velocity of the surface acoustic wave propagated on the annular surface portion around the Z-axis on the spherical body member 110, on that annular surface portion the comb-shaped electrode pieces 121, 122 being provided, is determined. Finally, the phase velocity is divided by the predetermined frequency, and the result of this division is used as the cycle "P".

As described above, the overlapping width "W" is less than or equal to half of the diameter of the spherical surface of the base member 110, and is greater than or equal to 1/100 of the radius of the spherical surface.

Figure 7:
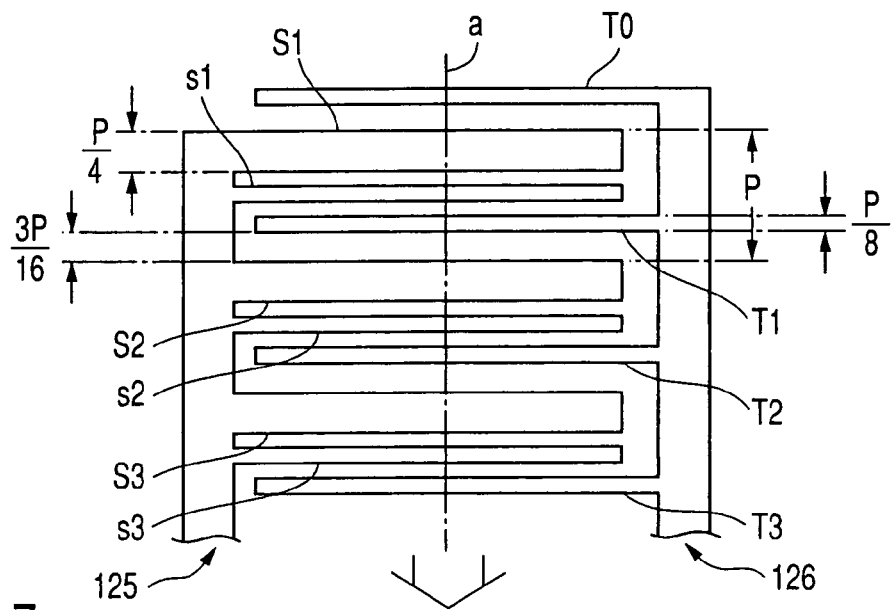
FIG. 7 is a schematic plan view of a modification of the comb-shaped electrode of FIG. 6.
Figure 8:
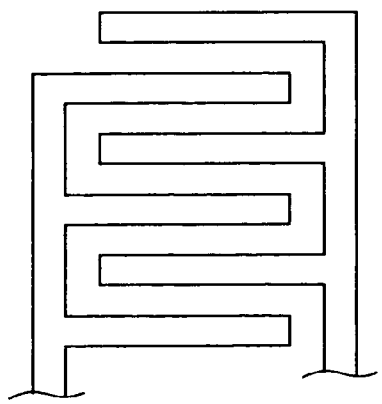
FIG. 8 is a plan view of pattern openings of a photomask for the comb-shaped electrode.

Next, a modification of the comb-shaped electrode pieces will be described. FIG. 7 is a schematic plan view of comb-shaped electrode pieces 125, 126 of the modification. In FIG. 7, all of the lines that are supposed as the latitude lines when the spherical base member 110 is supposed as the earth and the Z-axis is supposed as the geographic axis of the earth, are shown as the straight lines having the same length as to each other so that the base member 110 is shown as a square although actually it is the spherical shape.

The comb-shaped electrode piece 125 has a plurality of branches S1, s1, S2, s2, S3, s3, . . . which are arranged along the route "a". These branches extend along the longitude lines which are shown as the straight lines in FIG. 7. The branches S1 and s1, the branches S2 and s2, and the branches S3 and s3, . . . are respectively a pair. Further, these branches are arranged cyclically. All of a gap between the branch s1 and the branch S2, a gap between the branch S2 and the branch S3, . . . are equal to each other. Also, all of a gap between the branch S1 and the branch s1, a gap between the branch S2 and the branch s2, a gap between the branch S3 and the branch s3, . . . are equal to each other. If the branches S1 and s1 can be displaced along the route "a", these branches S1 and s1 can be respectively overlapped with the branches S2 and s2, the branches S3 and s3, . . . .

The comb-shaped electrode piece 126 has a plurality of branches T0, T1, T2, T3, . . . which are arranged along the route "a". These branches also extend along the longitude lines which are shown as the straight lines in FIG. 7. The branch T1 is disposed between the branch s1 and the branch S2, and the branch T2 is disposed between the branch s2 and the branch S3. The branch Ti (i=3, 4, 5, . . . ) including and after the branch T3 is disposed between the branch si and the branch Si+1, in the same way as each of the branches T1 and T2. The branch T0 is disposed such that the branches S1, s1 are positioned between the branch T0 and the branch T1. All gaps between the adjacent branches among the branches T0, T1, T2, T3, . . . are equal to each other. If the branch T0 can be moved along the route "a", the branch T0 can be overlapped with each of the branches T1, T2, T3, . . . .

The branches S1, s1, T1, the branches S2, s2, T3, and the branches S3, s3, T3 . . . are respectively a set. It is clear from the above explanation that the plural sets of these branches are arranged cyclically. The branches S1, s1, T1 form a unit in the branches arranged cyclically. Now, the dimensions of the comb-shaped electrode pieces 125, 126 will be described. As shown in FIG. 7, the cycle "P" is expressed by:

A cycle "P"=(the gap between the branch S1 and the branch S2)+(the width of the branch S1 in the direction along the route "a").

By using the "P", various dimensions of the comb-shaped electrode pieces 125, 126 are so set as described below:

the width of the branch S1 in the direction along route "a"="P"/4;

the width of the branch T1 in the direction along route "a"="P"/8; and the gap between the branch T1 and the branch S2=3"P"/16.

If the comb-shaped electrode pieces 125, 126 are formed as described above, the comb-shaped electrode pieces 125, 126 can output the surface acoustic wave in one direction (the direction shown by an arrow in FIG. 7) along the route "a".

The comb-shaped electrode pieces 121, 122 and 125, 126 of the embodiment and modification may be changed and modified variously. For example, the branch extending along the latitude line in the embodiment and modification may be changed to curve along the latitude line. When the comb-shaped electrode pieces are formed by a photo process in which exposure is carried out with a plate-shaped photo mask which has linearly and vertically extending holes and linearly and horizontally extending holes, each branch of the comb-shaped electrode piece formed by the photo process as described above curves along the latitude line. Such a photo mask as described above can be easily designed.

Further, the gap between the adjacent branches (for example, the gap between the branch S1 and the branch s1y and the gap between the branch s1 and the branch T1) or the gap of the sets of the branches (the gap between the branch T1 and the branch S2) or the cycle "P" may not be constant. As described above, in the sphere formed of quarts which is a crystal, the wavelength and phase velocity of the surface acoustic wave generated on the spherical surface is changed generally in accordance with the crystal orientation. If the gap between the adjacent branches, the cycle, and the like are set in accordance with the wavelength to be generated on the portion of the base member 110 at which the branches are positioned, the surface acoustic wave having a desired frequency can be excited efficiently. In particular, when the number of the branches are comparatively large and the comb-shaped electrode pieces are so formed as to make the phase variation which is necessary for traveling the surface acoustic wave around the base member 110 at one time be a multiple integer of $2\pi$ (rad), an electric signal processing apparatus using a surface acoustic wave element having the comb-shaped electrode pieces formed as described above can be used as a resonator having a strong output at a specific frequency.

A surface acoustic wave element for a wide band which has a flat plate shaped base member and a set of periodically arranged branches is conventionally known. If the structure of the conventional surface acoustic wave element is adapted to the spherical base member 110, surface acoustic waves over a wide wavelength range can be excited on the spherical base member 110. Only a surface acoustic wave having a wavelength, in which the collimating angle $\theta_{col}$ relating to the wavelength is greater than or equal to the overlapping width of the comb-shaped electrode pieces, can propagate on and around the spherical base member 110 without being diffused.

In an electric signal processing apparatus using the surface acoustic wave element of the present embodiment, a high frequency power source 123 is connected to the input terminals 120a, 120b. However, the present invention is not limited to such a structure of the electric signal processing apparatus. For example, in place of the high frequency power source 123, an antenna for receiving a high frequency wave may be connected to the input terminals 120a, 120b.

The electric signal processing apparatus connected to the antenna can be used as a frequency filter. When the antenna receives a high frequency wave, an electric field is generated at the comb-shaped electrode pieces 121, 122 and the surface acoustic wave is excited, in the same way as in the case where the high frequency power source 123 is connected. The comb-shaped electrode pieces 121, 122 are formed such that only a surface acoustic wave having a specific frequency is excited when an electric field is generated. Only the frequency component characterized by the shapes of the comb-shaped electrode pieces is excited. An electric signal corresponding to the surface acoustic wave is outputted from the output terminals.

Figure 9A:
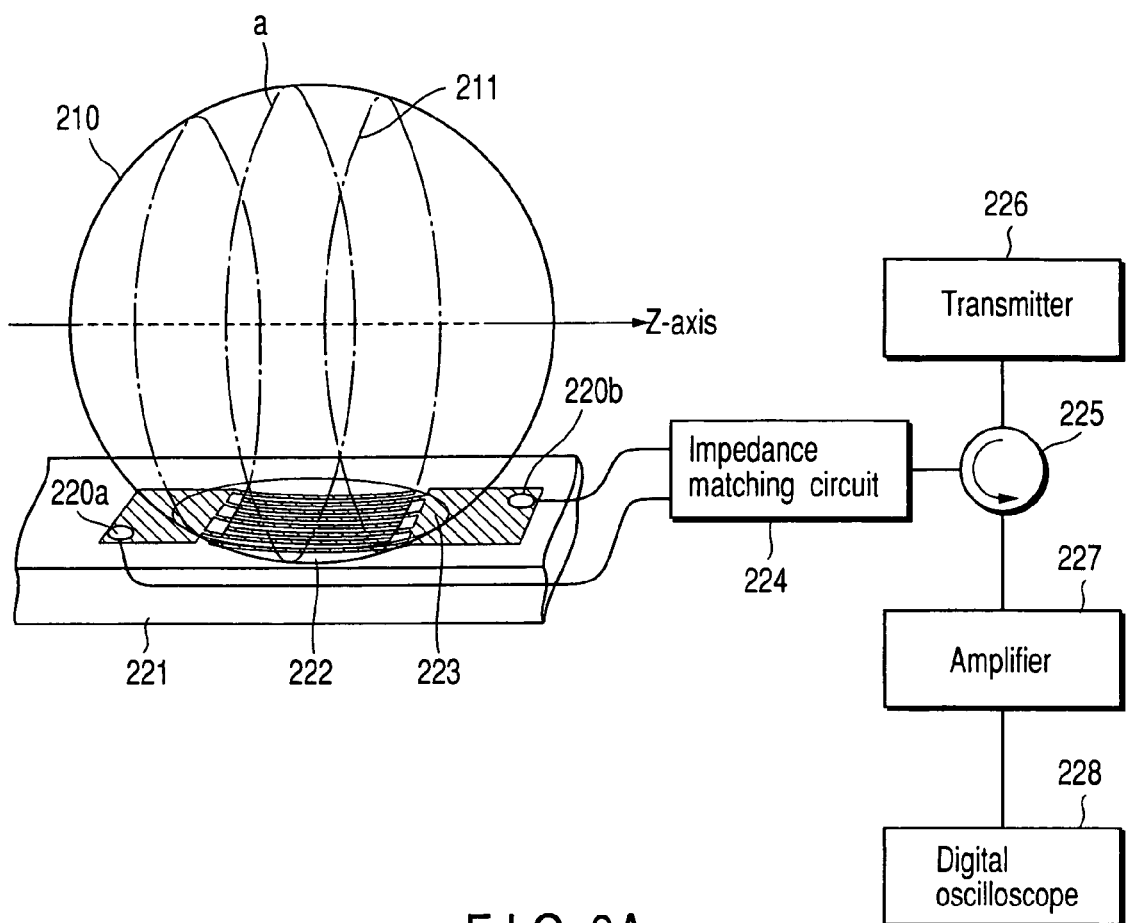
FIG. 9A shows a structure of a surface acoustic wave element of a second embodiment according to the present invention, and an electric signal processing apparatus using the surface acoustic wave element.

Next, a surface acoustic wave element according to a second embodiment of the present invention, an electric signal processing apparatus using the surface acoustic wave element and according to an embodiment of the present invention, and an environment evaluating apparatus using the electric signal processing apparatus and according to an embodiment of the present invention will be described. FIG. 9A shows a structure of the surface acoustic wave element and that of the electric signal processing apparatus using the surface acoustic wave element. The surface acoustic wave element has a spherical base member 210 formed of quarts of a single crystal. The base member 210 may be formed of a piezoelectric material of a single crystal such as LiNbO₃ of a single crystal, LiTaO₃ of a single crystal, or the like. The base member 210 is held on a base 221 formed of quarts glass. A concave portion 222 corresponding to one portion of the spherical surface of the base member 210 is provided on the base 221. The concave portion 222 is shown by looking through the base member 210. The base member 210 is fitted into the concave portion 222. In the present embodiment, each of a radius of the base member 210 and a radius of curvature of the concave portion 222 is 5 mm.

A comb-shaped electrode 223 shown by hatching is formed on the concave portion 222. The comb-shaped electrode 223 is used as the surface acoustic wave exciting means. The base member 210 and the comb-shaped electrode 223 configure the surface acoustic wave element. The comb-shaped electrode 223 has a chromium layer which is laminated on a surface of the base 221 and has a thickness of 500 Å, and a gold layer which is laminated on the chromium layer and has a thickness of 1500 Å. These layers are formed by thermal vapor deposition, and then are patterned by photolithography to form comb-shaped patterns. In addition to the comb-shaped patterns, a circuit (not shown) which is connected to the comb-shaped pattern and which is for generating an electric field, or the like is formed on the surface of the base member 110. The comb-shaped electrode 223 may be formed by other forming processes. For example, the comb-shaped electrode 223 may be formed by cutting a conductive foil into comb shapes and adhering the cut conductive foil on the concave portion 222. Further, the other forming processes may include a printing, a spattering, a sol-gel method, and the like.

When an electric signal is inputted to the comb-shaped electrode 223, the comb-shaped electrode 223 excites a surface acoustic wave which corresponds to the electric signal and which propagates along the annular surface. The comb-shaped electrode 223 excites the surface acoustic wave in this way, and also generates an electric signal corresponding to the surface acoustic wave when the surface acoustic wave propagating along the annular surface is received by the comb-shaped electrode.

A circulator 225, a transmitter 226, an amplifier 227, and a digital oscilloscope 228 are connected to the comb-shaped electrode 223 through an impedance matching circuit 224. The impedance matching circuit 224 is connected to input/output terminals 220a, 220b provided on the comb-shaped electrode 223. The input/output terminals 220a, 220b are used to input a predetermined electric signal to the comb-shaped electrode 223 and also used to output an electric signal generated by the comb-shaped electrode 223. The input/output terminals 220a, 220b are used as input/output portions. The electric signal inputted to the comb-shaped electrode 223 is generated by the transmitter 226, and the electric signal generated by the comb-shaped electrode 223 is inputted to the digital oscilloscope 228. The base member 210, the comb-shaped electrode 223, and the input/output terminals 220a, 220b are included in the electric signal processing apparatus. In the present embodiment, the electric signal processing apparatus forms a narrow-band frequency filter of 15.1 MHz.

The Z-axis of quarts base member 210 is arranged to be horizontal. The base member 210 is positioned with respect to the concave portion 222 such that branches of electrode pieces of the comb-shaped electrode 223 are arranged along a route "a". As described in the first embodiment, the route "a" is the equator when the Z-axis is supposed as the earth's axis.

The branch cycle of the comb-shaped electrode 223 is set as follows. Hereinafter, it is considered that the base member 210 is formed from an isotropic material. A value of a phase velocity of a Rayleigh wave of an X-axis propagation on a Y cut surface of the quarts crystal is 3160 m/s. This is considered to be a typical phase velocity. It is considered that an element, in which a surface acoustic wave of 15.1 MHz is excited and the wave number parameter becomes 150, is prepared. The wavelength of the surface acoustic wave is 0.209 mm from 3160 m/s÷15.1 MHz=209.3 μm. Accordingly, the branch cycle is set to 0.209 mm. Note that, because a circumferential length of the base member 210 is 31.415 mm, a radius of the base member 210 is 5.0 mm. Therefore, the wavelength of the surface acoustic wave is less than or equal to 1/10 of the radius of the spherical surface of the base member 210, as described above.

An overlapping width of the comb-shaped electrode 223 by which the surface acoustic wave is not diffused can be set as follows. The collimating angle $\theta_{col}$, which corresponds to the wave number parameter which is 150, is 7.0° from the above-described numeral calculation. From the definition of the collimating angle, the overlapping width is:

Overlapping width=(2×$\theta_{col}$/360)×circumferential length=(2×7.0/360)×31.415=1.22.

Accordingly, the overlapping width is set to 1.22 mm.

A resin thin film of 5000 Å is formed on the surface of quarts base member 210. The resin thin film is formed by forming a resist thin film pattern with a photo resist process, and by carrying out a film hardening process.

When voltage is applied to the comb-shaped electrode 223, the comb-shaped electrode 223 generates an electric field. This electric field passes through the resin thin film, and is applied to a region of the surface of the base member 210 facing the concave portion 222.

By the way, when a concave portion is not provided on the base, and comb-shape electrode is formed on a flat plate shaped base, and these comb-shape electrode face the base member, the electric field is applied to only a comparatively narrow region of the surface of the base member. On the other hand, if the concave portion 222 is provided as in the present embodiment, the electric field can be applied to a comparatively broad range of the base member 210.

Note that the resin thin film may be formed of a material whose properties vary in accordance with changes in the environment around the base member 210. Or, the resin thin film may be formed of a material whose properties vary by reacting with a specific material.

When an electric field is applied to the surface of the base member 210, a surface acoustic wave propagating along an annular surface portion 211 on the surface of the base member 210 is excited by the piezoelectric effect of quarts. The annular surface portion 211 extends along the route "a". A width of the annular surface portion 211 in the vicinity of the comb-shaped electrode 223 is substantially equal to the overlapping width of the comb-shaped electrode 223.

Resin particles whose particle diameter is 10 μm are scattered in the resin thin film between the surface of the base member 210 and the comb-shaped electrode 223. With this structure, the comb-shaped electrode 223 is spaced from the annular surface portion 211, and the excited surface acoustic wave is not reflected or diffused by the comb-shaped electrode 223 or the like.

If the electric field can be applied to the quarts base member 210 of a piezoelectric material, the gap between the comb-shaped electrode 223 and the annular surface portion 211 is preferably less than or equal to ¼ of the wavelength of the surface acoustic wave excited by the comb-shaped electrode 223. If the gap exceeds ¼ of the wavelength, it has been recognized that an amplitude of an electric field intensity based on a voltage gradient in the comb-shaped electrode becomes smooth and the intensity of the surface acoustic wave to be excited becomes extremely weak. In the present embodiment, the gap is about 10 μm, and the electrode piece cycle is 0.209 mm.

When predetermined conditions are satisfied, elastic wave is excited in the resin thin film as the resin thin film functions as a waveguide. An elastic wave of such a mode is included in the surface acoustic wave in the present invention.

Figure 10:
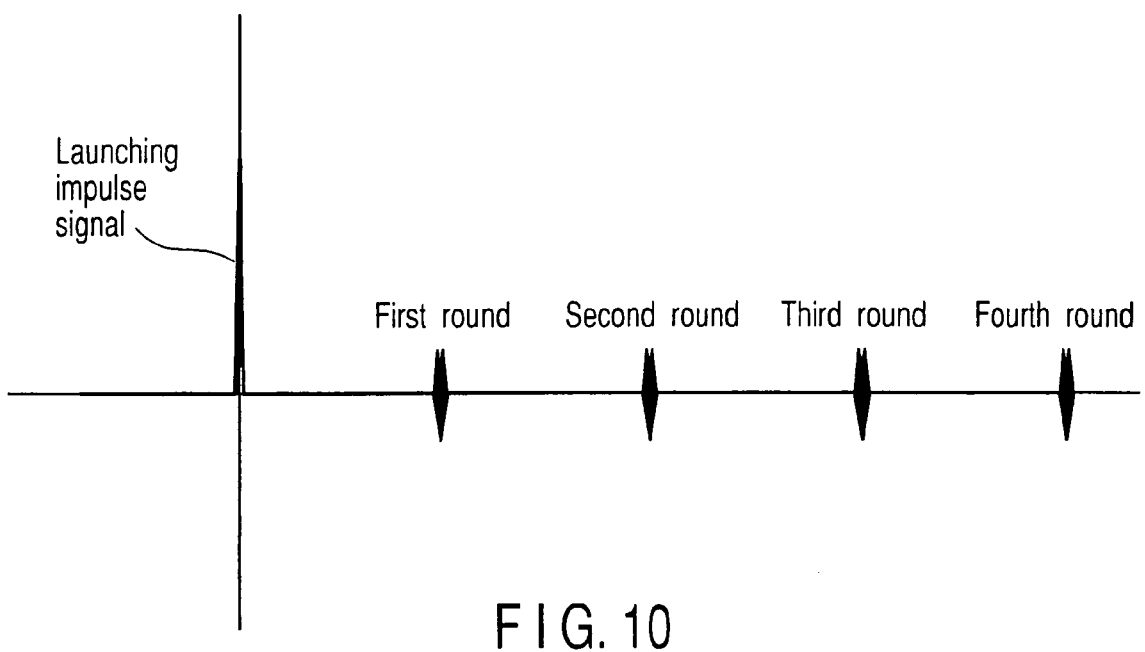
FIG. 10 shows waveforms of the surface acoustic waves measured by the surface acoustic wave element of FIG. 9A.

FIG. 10 shows waveformes of output signals measured through a low pass filter of 20 MHz when an impulse signal having a signal amplitude of 20V and a time width of 2 nanoseconds is inputted every 1 millisecond to the comb-shaped electrode 223 having the branch cycle and the overlapping width as described above. In FIG. 10, it could be recognized that the excited surface acoustic wave has extremely small noise signal, and circulates up to ten times.

Further, an electric signal in which frequencies of 15 MHz and 10 MHz were mixed is inputted to input/output terminals 220a, 220b of the electric signal processing apparatus used as the frequency filter. And, an electric signal outputted from the input/output terminals 220a, 220b is inputted in a digital oscilloscope 228, and frequency analysis of the electric signal is carried out. As a result, it is recognized that only the frequency component of 15 MHz is observed, and the frequency component of 10 MHz is eliminated.

Figure 9B:
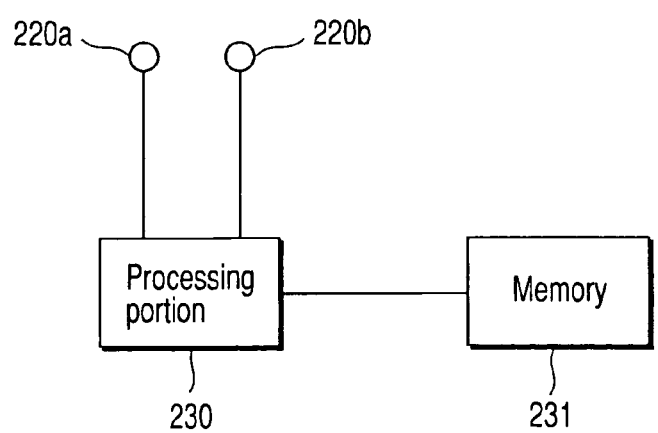
FIG. 9B shows a portion of an environment evaluating apparatus using the electric signal processing apparatus of FIG. 9A.

Next, the environment evaluating apparatus according to the embodiment of the present invention will be described. FIG. 9B is a schematic view showing a part of the environment evaluating apparatus. The environment evaluating apparatus has the above-described electric signal processing apparatus having the input/output terminals 220a, 220b. The environment evaluating apparatus is used for evaluating the environment around the base member 210. The environment evaluating apparatus includes a processing portion 230 which evaluates the environment around the base member 210 on the basis of at least one of the frequency of the electric signal outputted by the electric signal processing apparatus, the intensity of the electric signal, and the time passing from the time when the electric signal is inputted to the electric signal processing apparatus to the time when the electric signal is outputted by the electric signal processing apparatus. "Evaluating environment" is to obtain a physical quantity(s) for determining a state of the environment, such as temperature, humidity, or the like. The processing portion 230 is connected to the input/output terminals 220a, 220b.

By the way, it has been recognized that the time (delay time), passing from the time when the same signal as the impulse signal described with reference to FIG. 1 is inputted to the time when the signal transferred around the base member 210 four times is outputted from the electric signal processing apparatus, varies in accordance with the changes in temperature around the base member 210.

Returning to an explanation about the environment evaluating apparatus. A memory 231 storing a correspondence relationship between the delay time and the temperature in advance is connected to the processing portion 230. When the above-described impulse signal is inputted to the input/output terminals 220a, 220b, the processing portion 230 detects the delay time and obtains the degree of the temperature by using the correspondence relationship stored in the memory 231. In this way, the processing portion 230 obtains the temperature on the basis of the delay time.

Further, it is recognized that the output of the electric signal rapidly lowers when a predetermined electric signal is inputted to the electric signal processing apparatus used here and the base member 210 is humidified. This result is caused by the fact that dew condensation arose on the surface of the base member 210 so that the propagation of the surface acoustic wave is prevented. If a memory storing the correspondence relationship between the humidity and the output of the electric signal is used, the degree of the humidity can be obtained.

Further, the environmental evaluating apparatus can evaluate the environment around the base member 210 by utilizing the frequency.

Next, another embodiment of the environment evaluating apparatus will be described. The environment evaluating apparatus uses an electric signal processing apparatus having the surface acoustic wave element of the second embodiment. The environment evaluating apparatus is used for evaluating the environment in which the base member 210 is placed. The base member 210 is detachably held by the base 221. A reaction film whose hardness increases upon reacting with a specific chemical substance is formed on the surface of the base member 210. There are a large number of studies with respect to such a reaction film. At first, the base member 210 is placed in an environment in which the base member 210 is exposed to a chemical substance to be evaluated. At this time, a reaction occurs and the hardness of the reaction film increases in accordance with the concentration of the chemical substance or the like. Thereafter, the base member 210 is held on the base 221, and the frequency and velocity of the surface acoustic wave are inputted to the processing portion. The frequency of the surface acoustic wave and the velocity thereof are determined in accordance with the hardness of the reaction film. The processing portion can evaluate properties of the chemical substance such as the concentration thereof and the like by using the above described fact. That is, the environment in which the base member 210 is placed can be evaluated. When the apparatus is used for evaluation of a biological material in a living body, for example, a biological material of the digestive system, a large number of base members 210 are dosed orally. These base members 210 are taken out from excreta. In this case, the environment in which the base member 210 is placed is a space in the living body. At this time, there is no need to recover all of the orally dosed base members 210. The characteristics of the biological material can be evaluated in the same way as described above by using the recovered base members 210. Although a large number of base members 210 are required for such an evaluation, a cost required for this evaluation is relatively inexpensive because the base member 210 can be prepared extremely cheaply with an easy process. On the other hand, when the surface acoustic wave element of the first embodiment in which the comb-shaped electrode pieces 121, 122 are formed on the base member 110 is used for such an evaluation, the cost for such an evaluation is comparatively high.

Note that the comb-shaped electrode may be provided not on the base 221, but on the base member 210 as in the surface acoustic wave element of the first embodiment.

Figure 11:
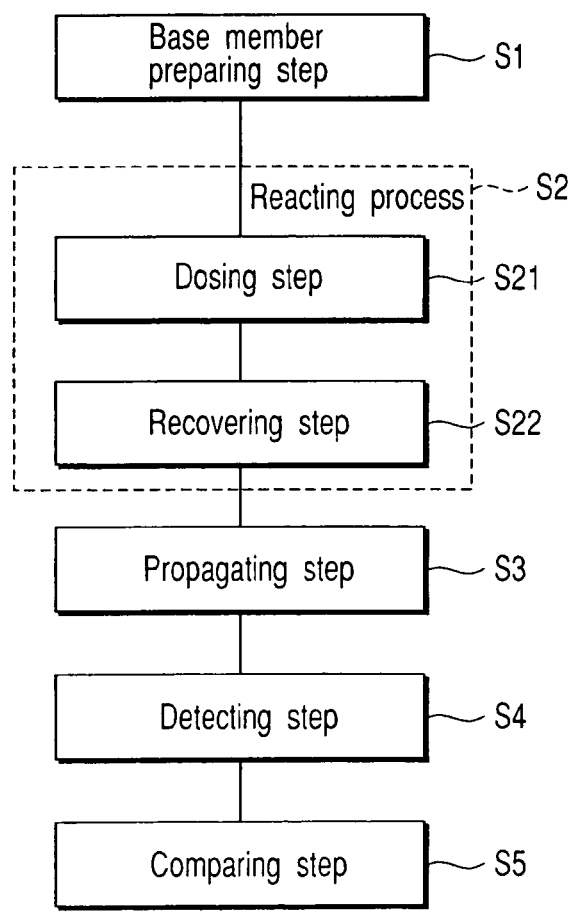
FIG. 11 shows a flow chart of an analyzing method using the surface acoustic wave element and electric signal processing apparatus of the first embodiment.

Next, an analyzing method of a first embodiment of the present invention will be described. FIG. 11 is a flowchart of the analyzing method. At first, a base member which has an annular surface formed by at least one portion of a spherical surface and continuing annularly is prepared (base member preparing step S1). In the present embodiment, a spherical base member formed of a single crystal of quarts which is a piezoelectric material is prepared. The base member has a reaction film formed on the surface of quarts and reacting with a predetermined intracorporeal material of a human body. That is, the reaction film is formed along the annular surface. The base member 210 of the surface acoustic wave element of the second embodiment is used as such a base member. In the present embodiment, the intracorporeal material is analyzed as a material to be inspected. The reaction film is used as a reacting portion. The reaction film is formed of a material whose hardness increases when reacting with the intracorporeal material. In this embodiment, the base member 210 is formed of quarts. However, the base member 210 may be formed of a single crystal of $LiNbO_3$, $LiTaO_3$, or the like which is the trigonal system being the same as quarts and which is the piezoelectric material.

Next, the reaction film is reacted with the internal material (reacting step S2). In order to react, the base member 210 is dosed orally (dosing step S21). At this time, a comparatively large number of base members 210 are dosed. The reaction film of the base member 210 reacts with the intracorporeal material and is hardened. These base members 210 are taken out from the excreta, and the base members 210 orally dosed in the step S21 are recovered (recovering step S22).

At this time, there is no need to recover all of the orally dosed base members 210. Although a large number of base members 210 are required in the reacting step S2, a cost required for the reacting step S2 is relatively inexpensive because the base member 210 can be prepared extremely cheaply with an easy process. A large number of base members 210 are required in the reacting step S2.

Next, the recovered base member 210 is placed on the concave portion 222 of the base 221 of the surface acoustic wave element of the second embodiment described with reference to FIG. 9A. Note that structural members which are substantially the same as the those described with reference to FIG. 9A are denoted by the same reference numerals as the those indicating the structural members corresponding to those of the surface acoustic wave element of the second embodiment, and detailed descriptions thereof will be omitted. When the base member 210 is placed on, the base member 210 is positioned such that the route "a" of the base member 210 extends in the direction in which the branches of the comb-shaped electrode 223 are arranged. As described above with reference to FIG. 5, the route "a" is the equator when the Z-axis of the base member 210 of quarts is considered as the earth's axis. The annular surface 211 is formed along the route "a". The base member 210 is appropriately positioned when the Z-axis is arranged horizontally. Marks are provided at portions corresponding to the north pole and the south pole when the Z-axis is considered as the earth's axis. The marks may be indents formed by etching the base member 210. After the positioning, the surface acoustic wave is made to propagate along the annular surface 211 (propagating step S3). Note that the base member 210 may be positioned such that any one of the routes b1, b2, and b3 on the base member 210 extends in the direction in which the branches of the comb-shaped electrode 223 are arranged.

Next, the surface acoustic wave propagated in the propagating step S3 is detected (detecting step S4).

Thereafter, the surface acoustic wave detected in the detecting step S4 and the surface acoustic wave propagating on the annular surface 211 of the base member 210 prepared in the base member preparing step S1 are compared with each other (comparing step S5). The latter surface acoustic wave propagates on the annular surface 211 of the base member 210 having the reaction film which has not reacted with the intracorporeal material. This surface acoustic wave is detected in advance. The hardness of the reaction film which reacted with the intracorporeal material varies in accordance with the properties of the intracorporeal material, for example, the concentration of the specific chemical substance. And, the frequency and the velocity of the surface acoustic wave vary in accordance with the hardness of the reaction film. That is, the differences between the frequency and the velocity of the surface acoustic wave detected in the detecting step S4 and those of the surface acoustic wave detected immediately after base member preparing step S1 vary in accordance with the properties of the intracorporeal material. By using this phenomenon, the properties of the chemical substance can be analyzed.

In the present embodiment, the intracorporeal material of a human body is analyzed as the material to be inspected. However, the intracorporeal material of an animal body excluding the human body may be analyzed as the material to be inspected.

Next, an analyzing method of a second embodiment of the present invention will be described. The analyzing method of the present embodiment is used for evaluating, for example, alkali concentration in a pipe. At first, a base member preparing step will be described. A spherical base member formed of a single crystal of quarts and having a diameter of 3 mm is prepared. The base member has a resist resin film formed on the surface of quarts and solved out in an alkali solution. That is, the resist resin film is formed along the annular surface. The resist resin film forms a reacting portion. Marks are provided at portions corresponding to the north pole and the south pole when the Z-axis of the base member of quarts is considered as the earth's axis.

In the following reacting step, the base member is put into a pipe, and the resist resin film is reacted with the alkali solution in the pipe. The resist resin film is solved out in the alkali solution, and the thickness of the film is reduced. After reaction, the base member is recovered from the pipe.

After recovery, a propagating step, a detecting step, and a comparing step are carried out in the same way as in the analyzing method of the first embodiment. In the present embodiment, the alkali solution in the pipe is analyzed by the fact that the frequency and the velocity of the surface acoustic wave vary in accordance with the thickness of the resist resin film.

A reacting portion which is hardened or solved out is used in the above-described first or second embodiment. However, the present invention is not limited thereto. Various reacting portions which is separated from, combined with, decomposing, etc. the material to be inspected, are included.

Next, a surface acoustic wave element of a third embodiment of the present embodiment will be described. A main part of the present embodiment is basically the same as a main part of the second embodiment. In the present embodiment, structural members which are substantially the same as those described with reference to FIG. 9A of the second embodiment are denoted by the same reference numerals as those indicating the structural members corresponding to those of the second embodiment, and detailed description thereof will be omitted.

Figure 12:
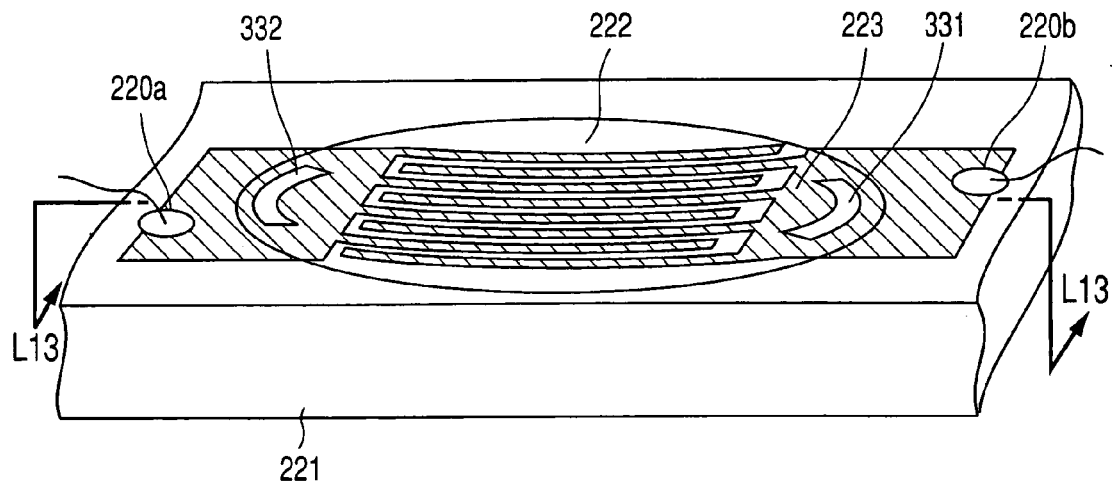
FIG. 12 is a perspective view of a support of a surface acoustic wave element of a third embodiment according to the present invention.

The present embodiment is different from the second embodiment in that a resin thin film is not provided on the base member 210. FIG. 12 is a perspective view of the base member 221. Spacers 331, 332 for spacing the comb-shaped electrode 223 from the base member 210 are provided on the base 221 in place of the resin particles. The spacers 331, 332 are provided by hardening a resist resin. The spacers 331, 332 are disposed in both sides of the branches arranged in the comb-shape in the comb-shaped electrode 223, and are provided so as not to affect the propagation of the surface acoustic wave.

Figure 13:
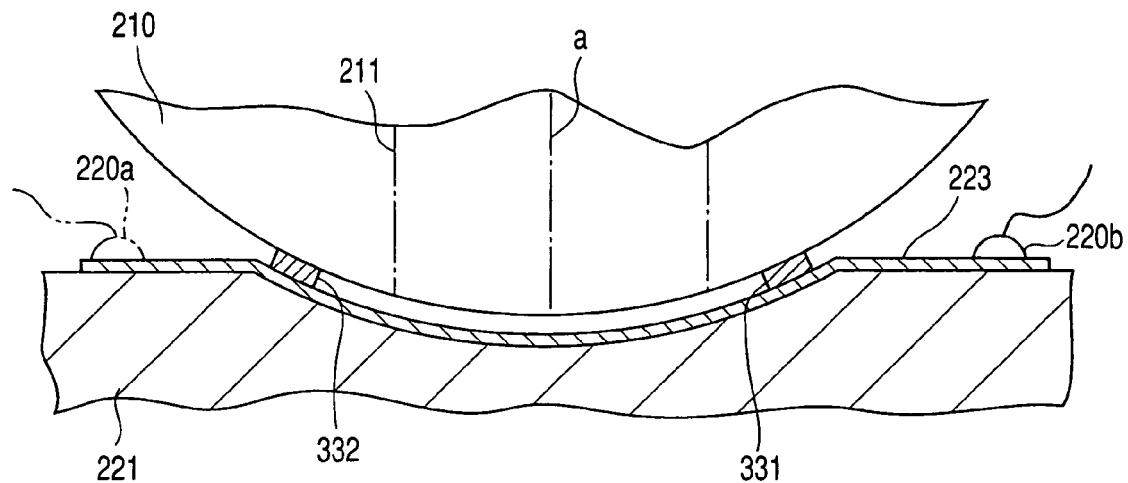
FIG. 13 is a sectional view of the support taken along a cross-section line of L13—L13 in FIG. 12 with a part of a spherical base member supported thereon.

FIG. 13 is a sectional view in which the base 221 is cut along a cross-section line L13—L13 in FIG. 12, and the base member 210 is held by the spacers 331, 332. The cross-section line L13—L13 goes through the two spacers 331, 332, and extends in a direction perpendicular to a direction in which the comb-shaped electrode 223 outputs the surface acoustic wave. The gap is preferably less than or equal to ¼ of the branch cycle of the comb-shaped electrode 223 in the same way as in the second embodiment. In the present embodiment, the gap is 10 µm.

Two portions of the base member 210 with which the two spacers 331, 332 are in contact at both sides of the annular surface 211, and these portions are spaced from the annular surface 211. With this structure, the surface acoustic wave can propagate on the annular surface 211 without being diffused or being reflected.

In the present embodiment, the two spacers are provided in the both sides of the comb-shaped electrode 223. However, the present invention is not limited thereto. For example, two spacers may be provided in each of the both sides. Or, fine resin particles may be dispersed between the base member 210 and the comb-shaped electrode 223 to make a gap between the comb-shaped electrode 223 and the annular surface 211.

Figure 14:
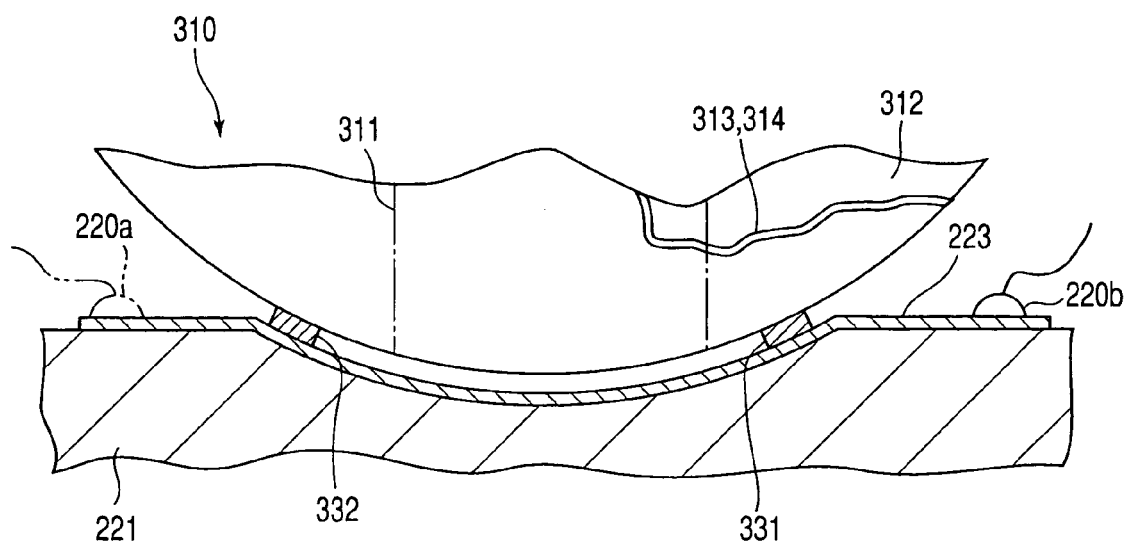
FIG. 14 is a sectional view of a support of a surface acoustic wave element which is a modification of the third embodiment and is shown like that in FIG. 13.

Next, a modification of the above-described third embodiment will be described. FIG. 14 is a sectional view of the modified surface acoustic wave element viewed from the same standpoint as in FIG. 13. The surface acoustic wave element of the present embodiment has a base member 310 in place of the base member 210. The base member 310 has a spherical member 312 formed of a glass material which is an isotropic material, a gold film 313 whose thickness is 1000 Å and which covers the spherical member 312, and a Z-axis orientation film 314 of ZnO covering the gold film 313. In FIG. 14, the gold film 313 and the orientation film 314 are shown such that they are partially eliminated from the surface of the spherical member 312. The orientation film 314 is made of a piezoelectric material. That is, one portion of the base member 310 is formed of the piezoelectric material.

The gold film 313 is formed by the vapor deposition or the like. The orientation film 314 is formed by DC spattering. The orientation film can be formed on the annular region circling around the base member 310 by carrying out the spattering while rotating the base member 310. By carrying out the spattering as described above, the orientation film can be formed over the entire surface of the base member 310. Conventional techniques can be basically used with respect to a concentration of gas, a value of a DC high tension voltage, and the like, used for DC spattering, and a method for preparing a mask for deposition.

When an electric field is applied to the base member 310 by the comb-shaped electrode 223, the Z-axis orientation film 314 of ZnO is vibrated by a piezoelectric effect. As a result, a surface acoustic wave propagating along the annular surface 311 of the base member 310 is excited. The annular surface 311 extends between the spacer 331 and the spacer 332 in a direction in which the branches of the comb-shaped electrode 223 are arranged. The annular surface 311 is spaced from the spacers 331, 332. Therefore, the surface acoustic wave can propagate on the annular surface 311 without being diffused or being reflected. Note that the annular surface 311 is not along a specific route based on properties of the material of the base member 310, and this is different from the case in which the base member is formed of quarts as described above with reference to FIG. 5. However, the annular surface 311 extends along the maximum circumferential line of the base member 310.

In the present embodiment, the overlapping width of the comb-shape electrode 223 is 2 mm, and the branch cycle is 350 µm. The height of each of the spacers 331, 332, i.e., the gap between the comb-shape electrode 223 and the annular surface 311, is 10 µm. This is less than or equal to ¼ of the branch cycle.

In the present embodiment, the two spacers are provided in both sides of the comb-shaped electrode 223. However, the present invention is not limited thereto. For example, two spacers may be provided in each of the both sides. Or, fine resin particles may be scattered between the base member 310 and the comb-shaped electrode 223 to provide a gap between the comb-shaped electrode 223 and the annular surface 311.

Next, a surface acoustic wave element of a fourth embodiment of the present embodiment will be described. A main part of the present embodiment is basically the same as that of the third embodiment. In the present embodiment, structural members which are substantially the same as those of the third embodiment described above with reference to FIGS. 12 and 13 are denoted by the same reference numerals as those denoting the corresponding structural members of the third embodiment, and detailed descriptions thereof will be omitted.

Figure 15:
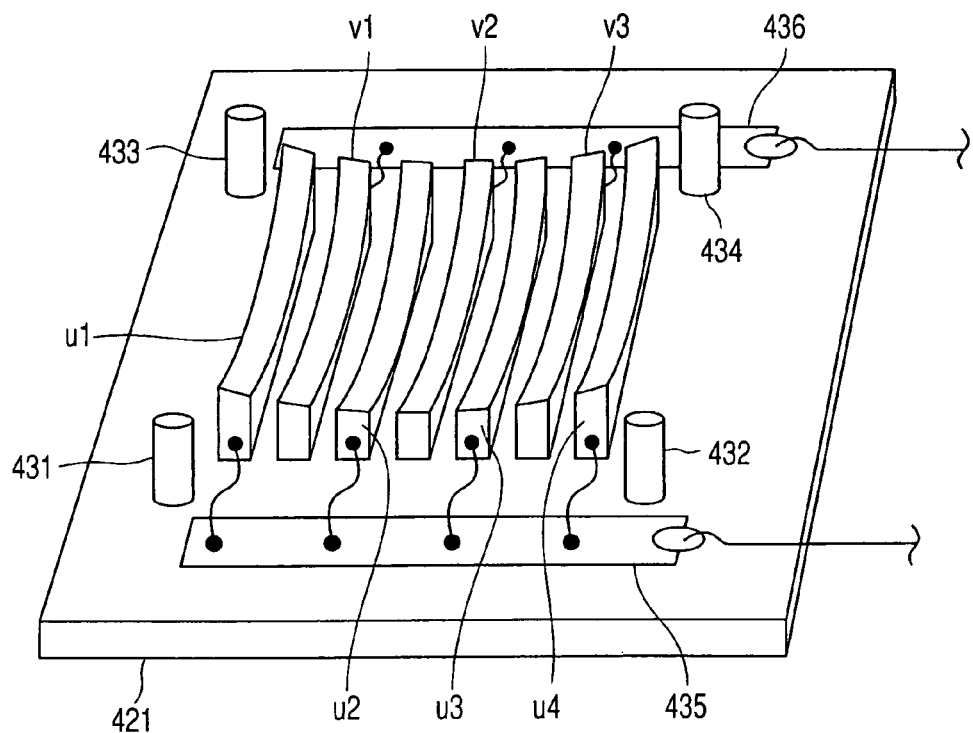
FIG. 15 is a perspective view of a support of a surface acoustic wave element of a fourth embodiment according to the present invention.

In the present embodiment, a base 421 is used in place of the base 221 of the third embodiment. FIG. 15 is a perspective view of the base 421. Square sectioned branches u1, v1, u2, v2, u3, v3, and u4 are arranged in this order on an upper surface of the base 421 and are projected from the upper surface in the vertical direction. These branches form a comb-shaped electrode. Upper surfaces of these branches form a concave surface having a shape which is along one portion of the spherical surface of the base member 210. The adjacent branches among these branches u1, v1, u2, v2, u3, v3, and u4 are respectively connected to other terminals. The branches u1, u2, u3, and u4 are connected to one terminal 435, and the branches v1, v2, and v3 are connected to another terminal 436. Square sectioned projections for these branches, together with the base 421, are formed by cutting a glass epoxy material, and upper surfaces of these projections are plated with copper to make the branches. The terminals 435, 436 are connected to the impedance matching circuit 224 through a predetermined circuit. These branches u1, v1, u2, v2, u3, v3, and u4 and the terminals 435, 436 are used as a surface acoustic wave element exciting means.

Four holding members 431, 432, 433, and 434 for holding the base member 210 are provided on the upper surface of the base 421. When the base member 210 is held by the holding members 431, 432, 433, and 434, the upper surfaces of the branches u1, v1, u2, v2, u3, v3, and u4 face the surface of the base member 210 with a gap therebetween. When an electric field is applied to the base member 210 by these branches, a surface acoustic wave propagating along the annular surface 211 of the base member 210 is excited. The annular surface 211 extends along the maximum circumferential line. The comb-shaped electrode formed by these branches faces the annular surface 211 with the gap therebetween. The gap is less than or equal to ¼ of the branch cycle of the comb-shaped electrode. The holding members 431, 432, 433, are 434 are positioned in the both sides of the annular surface 211.

If the surface acoustic wave element is structured in this way, the same technical advantages as those obtained by the third embodiment can be obtained.

In the present embodiment, the comb-shaped electrode is formed by the seven branches u1, v1, u2, v2, u3, v3, and u4. However, the number of the branches may be two through six, or may be greater than or equal to eight.

Figure 16A:
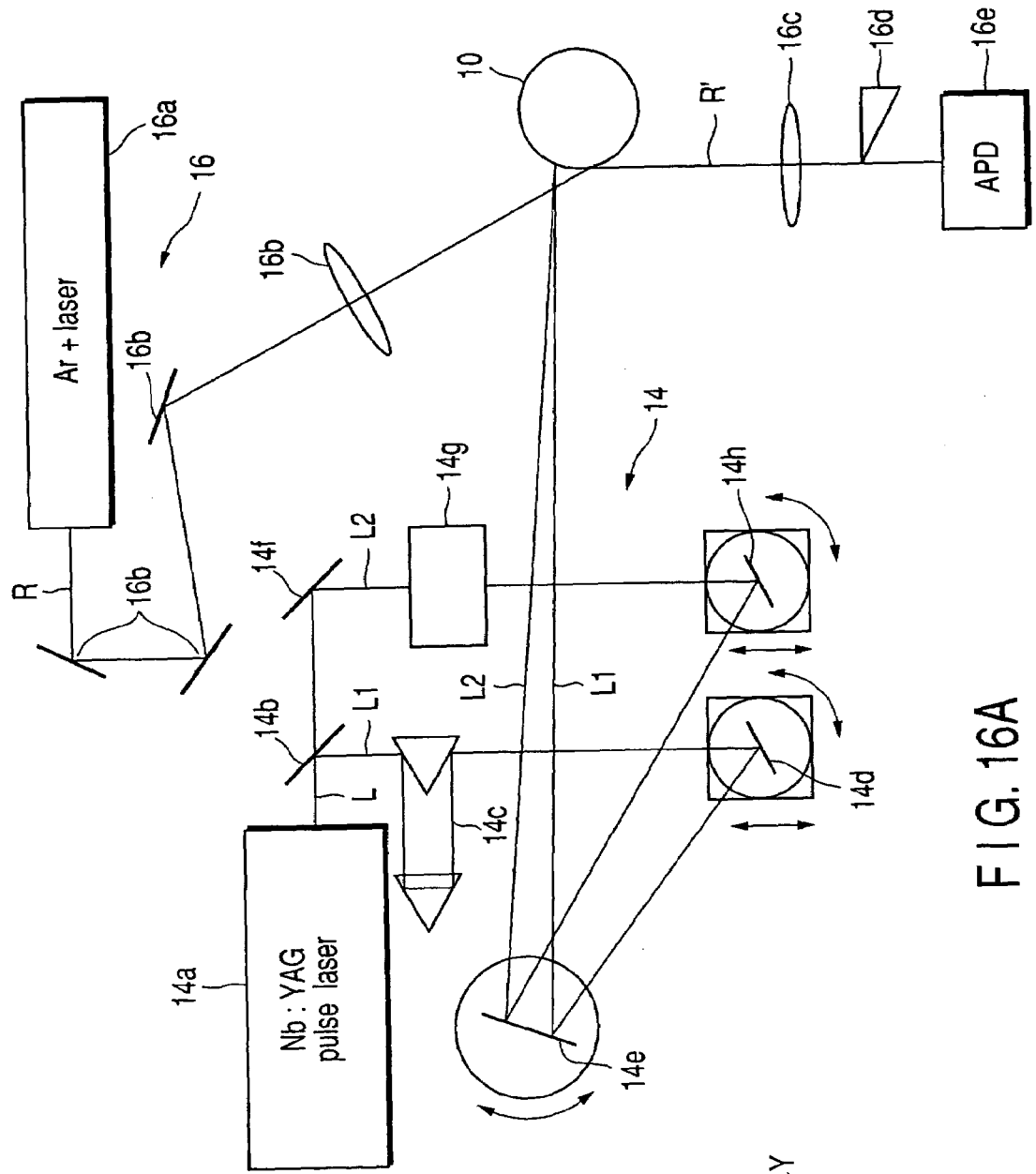
FIG. 16A is a plan view schematically showing a whole of an apparatus used for exciting and detecting a surface acoustic wave.
Figure 16B:
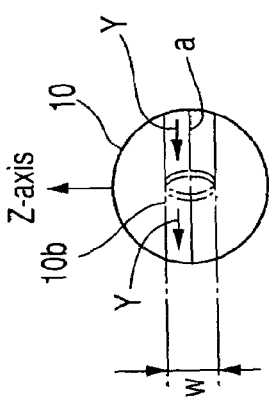
FIG. 16B is an enlarged side view of a base member used in the apparatus shown in FIG. 16A.

Next, a surface acoustic wave element of a fifth embodiment of the present invention will be described. FIG. 16A is a plan view in which an entire apparatus used for exciting and detecting a surface acoustic wave is schematically shown. FIG. 16B is an enlarged side view of a spherical base member 10.

In the present embodiment, the spherical base member 10 is formed of a single crystal of $LiNbO_3$. However, the base member 10 may be formed of other single crystals belonging to the trigonal system, such as quarts, $LiTaO_3$, and the like. An annular surface 10b of the base member 10 of $LiNbO_3$ can be formed along the route "a" on the equator defined while the Z-axis is considered as the earth's axis, and along the routes b1, b2, and b3 on the longitude lines in the same way as that in the case of the base member 110 formed of quarts in the first embodiment shown in FIG. 5. The surface acoustic wave may be propagated along at least two routes among the routes b1, b2, and b3. In the present embodiment, the annular surface 10b is formed along the route "a".

Laser beam is projected from a laser beam projecting means 14 onto a predetermined range "w" in a direction, which is along the surface of the base member 10 and which is perpendicular to the route "a", so as to generate a surface acoustic wave. The predetermined range "w" defines the annular surface 10b.

The laser beam projecting means 14 splits a laser beam "L" projected from a YAG pulse laser light source 14a into two, and leads one split laser beam "L1" to a first sub rotating and reflecting mirror 14d via a delay element 14c, and leads the laser beam "L1" from the first sub rotating and reflecting mirror 14d to a main rotating and reflecting mirror 14e, and projects the laser beam "L1" from the main rotating and reflecting mirror 14e onto the predetermined range "w" on the outer peripheral surface of the base member 10. The other split laser beam "L2" is led to a second sub rotating and reflecting mirror 14h via a reflecting mirror 14f and a Bragg cell 14g, and further led from the second sub rotating and reflecting mirror 14h to the main rotating and reflecting mirror 14e, and is projected from the main rotating and reflecting mirror 14e onto the predetermined range "w" on the outer peripheral surface of the base member 10.

The two laser beams "L1", "L2" are positioned by the first sub rotating and reflecting mirror 14d, the second sub rotating and reflecting mirror 14h, and the main rotating and reflecting mirror 14e so as to generate interference fringes with thermoelasticity effect in the predetermined range "w".

A gold film used as a laser light absorbing member is applied on a surface of the base member 10 including the annular surface 10b. The laser light absorbing member forms a surface acoustic wave exciting means. When the laser beams "L1", "L2" are overlapped in the predetermined range "w" on the surface of the base member, interference fringes are generated. At this time, the laser beams "L1", "L2" are absorbed in the gold film. As a result, a surface acoustic wave is excited in the predetermined range "w" by the thermoelasticity effect. The excited surface acoustic wave rounds or orbits in the direction shown by an arrow "Y" along the route "a" along the annular surface 10b without being diffused.

In the present embodiment, the laser light absorbing member is used. However, when the base member is formed of a material absorbing laser light, and the laser light is absorbed in the surface of the base member, and a surface acoustic wave is excited, it is possible to not use the laser light absorbing member.

The method in which a surface acoustic wave is generated by utilizing interference fringe of laser beams as described above has been known as the Scanning Interference Fringes (SIF) method (H.Nishino, Y.Tsukahara, Y.Nagata, T.Koda, and K.Yamanaka; Appl. Phys. Left. 32, 1993, 2036: and K.Yamanaka, O.Kolosov, H.Nishino, Y.Tsukahara, Y.Nagata, and T.Tosa; J.Appl. Phys. 74, 1993, 6511).

Since the surface acoustic wave element of the present embodiment utilizes the interference fringes of laser beams, the surface acoustic wave element is free from a thing such as a comb-shaped electrode, which is in contact with the annular surface and which diffuses or reflects the surface acoustic wave in the annular surface as in the first embodiment. A wavelength of the surface acoustic wave excited by using the interference fringes corresponds to a gap in the interference fringes.

Since the gap in the interference fringes can be easily changed, a surface acoustic wave having a desired wavelength can be comparatively easily excited. On the other hand, in order to excite a surface acoustic wave having another wavelength in place of the specific wavelength in the surface acoustic wave element using the comb-shaped electrode, it is necessary to prepare another comb-shaped electrode.

The apparatus shown in FIG. 16A further has a detecting means 16 for detecting, without being in contact with the base member 10, a surface acoustic wave which is generated in the annular surface 10b of the spherical base member 10 and which propagates as described above on the annular surface 10b. The detecting means 16 has an Ar laser light source 16a; various optical members 16b leading a laser beam R projected from the Ar laser light source 16a to a position on the annular surface 10b of the spherical base member 10, the position being apart from a position on which the two laser beams "L1", "L2" are projected; and an optical member 16c and a knife edge 16d, for leading the laser beam R' reflected on the above-described apart position to an Ar laser light detector (APD) 16e.

Operations of the apparatus shown in FIG. 16A will be described. The two YAG laser beams L1, L2 each of which has a diameter of 3 mm are directed to the predetermined range w (FIG. 16B) on the surface of the base member 10 at substantially right angles. As compared with a frequency of one YAG laser beam L1, a frequency of another YAG laser beam L2 is deviated by only 30 MHz from the frequency of one YAG laser beam L1 by using the Bragg cell 14g. An interference of the two laser beams L1, L2 with the different frequencies forms scanning interference fringes on a portion to which the two laser beams L1, L2 are projected in the predetermined range "w" (FIG. 16B) on the surface of the base member 10. By a mechanical adjusting means such as the first sub rotating and reflecting mirror 14d, the second sub rotating and reflecting mirror 14h, and further the main rotating and reflecting mirror 14e, an average gap in the interference fringes is adjusted to be equal to the wavelength of the surface acoustic wave, and a scanning speed of the interference fringes is adjusted to be equal to an average phase velocity of the surface acoustic wave, and phase matching between the interference fringes and the surface acoustic wave is carried out. Each of the laser beams "L1", "L2" has a long pulse of about 100 ns especially designed for achieving a long interaction time between the interference fringes and the surface acoustic wave. The long interaction time suppresses bulk acoustic waves (BAW) (K. Yamanaka: Jpn. Appl. Phys. 36, 1997, 2939). On the other hand, it is considered that it is indispensable for a selective generation and amplification of a surface acoustic wave.

The surface acoustic wave repeatedly propagates on the annular surface 10b (FIG. 16B) of the predetermined range "w" along the route "a" (FIG. 16B) of the base member 10 which is perpendicular to the interference fringes. Next, the surface acoustic wave is detected by a detecting means 16 using an optical knife edge method using an Ar laser light condensed at a position which is apart by a predetermined distance from the interference fringes.

Note that the present invention is not limited to the above described embodiments, and various modifications and applications may be possible without departing from an idea of the present invention.

The surface acoustic wave element of the present invention is suitable for a delay line, an oscillating element for a transmitter, a resonating element, or the like. The electric signal processing apparatus of the present invention is suitable for a filter for selecting frequencies, or the like. The environment evaluating apparatus of the present invention is suitable for a chemical sensor, a biosensor, or the like. The analyzing method of the present invention is suitable for analyzing a material to be inspected such as a chemical substance, a biological material, or the like.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A surface acoustic wave element comprising:
   a base member having an annular surface formed by at least one portion of a spherical surface and continuing annularly, and being made of a single crystal;
   a surface acoustic wave exciting unit which excites a surface acoustic wave propagating along the annular surface;
   the annular surface being formed so as to be along a predetermined route determined by a crystal orientation of the single crystal making up the base member;
   a crystal system of the single crystal making the base member being a trigonal system; and
   the predetermined route determined by the crystal orientation including an intersection line between the spherical surface and a plane passing through a center of the spherical surface and crossing a Z-axis of the single crystal of the trigonal system at right angles.

2. A surface acoustic wave element according to claim 1, wherein at least one portion of the base member is made of a piezoelectric material.

3. A surface acoustic wave element according to claim 1, wherein the single crystal making the base member is quartz.

4. A surface acoustic wave element according to claim 1, wherein the single crystal making the base member is a single crystal selected from a group consisting of a single crystal of $LiNbO_3$ and a single crystal of $LiTaO_3$.

5. A surface acoustic wave element according to claim 1, wherein a wavelength of the surface acoustic wave excited by the acoustic wave exciting unit is less than or equal to $1/10$ of a radius of the spherical surface of the base member.

6. A surface acoustic wave element according to claim 1, wherein the acoustic wave exciting unit is provided so as to be along the annular surface, and includes a comb-shaped electrode connected to a high frequency power source.

7. A surface acoustic wave element according to claim 6, wherein the branches of the comb-shaped electrode face each other for over a length which is less than or equal to half of a diameter of the spherical surface of the base member and which is greater than or equal to $1/100$ of a radius of the spherical surface.

8. A surface acoustic wave element according to claim 1, wherein the acoustic wave exciting unit is provided on the annular surface, and has a laser beam absorbing member which absorbs laser beam and excites the surface acoustic wave by a thermoelastic effect.

9. A surface acoustic wave element, comprising:
   a base member having an annular surface formed by at least one portion of a spherical surface and continuing annularly, and being made of a single crystal;
   a surface acoustic wave exciting unit which excites a surface acoustic wave propagating along the annular surface;
   the annular surface being formed so as to be along a predetermined route determined by a crystal orientation of the single crystal making up the base member;
   a crystal system of the single crystal making the base member is a trigonal system; and
   the predetermined route determined by the crystal orientation including an intersection line between the spherical surface and a plane passing through a center of the spherical surface and being in parallel to a Z-axis of the single crystal of the trigonal system.

10. A surface acoustic wave element according to claim 9, wherein at least one portion of the base member is made of a piezoelectric material.

11. A surface acoustic wave element according to claim 9, wherein the single crystal making up the base member is quartz.

12. A surface acoustic wave element according to claim 9, wherein the single crystal making up the base member is a single crystal selected from a group consisting of a single crystal of $LiNbO_3$ and a single crystal of $LiTaO_3$.

13. A surface acoustic wave element according to claim 9, wherein a wavelength of the surface acoustic wave excited by the acoustic wave exciting unit is less than or equal to $1/10$ of a radius of the spherical surface of the base member.

14. A surface acoustic wave element according to claim 9, wherein the acoustic wave exciting unit is provided so as to be along the annular surface, and includes a comb-shaped electrode connected to a high frequency power source.

15. A surface acoustic wave element according to claim 14, wherein the branches of the comb-shaped electrode face each other for over a length which is less than or equal to half of a diameter of the spherical surface of the base member and which is greater than or equal to $1/100$ of a radius of the spherical surface.

16. A surface acoustic wave element according to claim 9, wherein the acoustic wave exciting unit is provided on the annular surface, and has a laser beam absorbing member which absorbs laser beam and excites the surface acoustic wave by a thermoelastic effect.

17. An electric signal processing apparatus, comprising:
a surface acoustic wave element according to any one of claims 2, 3–1, 5, 8, and 9–16;
a detecting unit which detects the surface acoustic wave propagating along the annular surface; and
an output portion which outputs an electric signal corresponding to the surface acoustic wave detected by the detecting unit.

18. An environment evaluating apparatus, comprising:
an electric signal processing apparatus according to claim 17; and
a processing portion which evaluates an environment around the base member or an environment in which the base member is placed, on the basis of at least one of a change in frequency of the electric signal outputted by the output portion of the electric signal processing apparatus, a change in an intensity of the electric signal outputted by the output portion of the electric signal processing apparatus, and time elapsing from the time when the surface acoustic wave is excited by the surface acoustic wave exciting unit to the time when the surface acoustic wave is detected by the detecting unit and the output portion outputs an electric signal corresponding to the detected signal after the surface acoustic wave propagates along the annular surface of the base member for a predetermined time.

19. A surface acoustic wave element, comprising:
a base member which has an annular surface formed by at least one portion of a spherical surface and continuing annularly, and which is made of a single crystal;
a surface acoustic wave exciting unit which excites a surface acoustic wave propagating along the annular surface; and
the acoustic wave exciting unit being provided on the annular surface, and having a laser beam absorbing member which absorbs laser beam and excites the surface acoustic wave by a thermoelastic effect.

* * * * *

UNITED STATES PATENT AND TRADEMARK OFFICE
CERTIFICATE OF CORRECTION

PATENT NO. : 7,170,213 B2
APPLICATION NO. : 10/819365
DATED : January 30, 2007
INVENTOR(S) : Kazushi Yamanaka et al.

It is certified that error appears in the above-identified patent and that said Letters Patent is hereby corrected as shown below:

Column 25, Line 42, after "element" insert --,--.

Column 27, Line 3, change "2, 3-1, 5, 8, and 9-16" to --1-16--.

Signed and Sealed this

Eighth Day of April, 2008

JON W. DUDAS
*Director of the United States Patent and Trademark Office*